(12) United States Patent
Browning et al.

(10) Patent No.: US 8,287,874 B2
(45) Date of Patent: *Oct. 16, 2012

(54) SOLUBLE LYMPHOTOXIN-BETA RECEPTORS AND ANTI-LYMPHOTOXIN RECEPTOR AND LIGAND ANTIBODIES AS THERAPEUTIC AGENTS FOR THE TREATMENT OF IMMUNOLOGICAL DISEASES

(75) Inventors: Jeffrey L. Browning, Brookline, MA (US); Paula S. Hochman, Brookline, MA (US); Paul D. Rennert, Millis, MA (US); Fabienne Mackay, Watertown, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 310 days.

This patent is subject to a terminal disclaimer.

(21) Appl. No.: 12/813,029

(22) Filed: Jun. 10, 2010

(65) Prior Publication Data

US 2012/0156214 A1    Jun. 21, 2012

Related U.S. Application Data

(63) Continuation of application No. 11/891,847, filed on Aug. 13, 2007, now Pat. No. 7,744,891, which is a continuation of application No. 09/299,139, filed on Apr. 23, 1999, now Pat. No. 7,255,854, which is a continuation of application No. PCT/US97/19436, filed on Oct. 24, 1997.

(60) Provisional application No. 60/029,060, filed on Oct. 25, 1996.

(51) Int. Cl.
*A61K 39/395* (2006.01)

(52) U.S. Cl. .................................. 424/178.1; 424/130.1

(58) Field of Classification Search ......................... None
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 4,816,567 A | 3/1989 | Cabilly et al. | |
| 5,225,538 A | 7/1993 | Capon et al. | |
| 5,661,004 A | 8/1997 | Browning et al. | |
| 5,670,149 A | 9/1997 | Browning et al. | |
| 5,795,964 A | 8/1998 | Browning et al. | |
| 5,925,351 A | 7/1999 | Browning et al. | |
| 6,312,691 B1 | 11/2001 | Browning et al. | |
| 6,403,087 B1 | 6/2002 | Browning et al. | |
| 6,669,941 B1 | 12/2003 | Browning et al. | |
| 7,001,598 B2 | 2/2006 | Browning et al. | |
| 7,030,080 B2 | 4/2006 | Browning et al. | |
| 7,060,667 B1 | 6/2006 | Browning et al. | |
| 7,255,854 B1 | 8/2007 | Browning et al. | |
| 2002/0197254 A1 | 12/2002 | Browning et al. | |
| 2005/0037003 A1 | 2/2005 | Browning et al. | |
| 2005/0281811 A1 | 12/2005 | Browning et al. | |
| 2006/0280722 A1 | 12/2006 | Browning et al. | |
| 2007/0116668 A1 | 5/2007 | Browning et al. | |

FOREIGN PATENT DOCUMENTS

| | | |
|---|---|---|
| EP | 0840616 B1 | 10/2004 |
| WO | 92/00329 A1 | 1/1992 |
| WO | 94/46679 | 3/1994 |
| WO | 94/13808 A2 | 6/1994 |
| WO | 97/03678 A1 | 2/1997 |
| WO | 97/03687 A1 | 2/1997 |
| WO | 97/20063 A1 | 6/1997 |

OTHER PUBLICATIONS

MacLennan, I.C.M., "The Structure and Function of Secondary Lymphoid Tissues,"Clinical Aspects of Immunology, 5th Edition, Edited by P.J. Lachmann et al., Blackwell Scientific Publications, Inc., vol. 1, Chapt. 2, pp. 13-30 (1993).
Maeda, Kunihiko et al., "Murine Follicular Dendritic Cells and Low Affinity Fc Receptors for IgE (FceRII)," The Journal of Immunology, vol. 148(8):2340-2347 (1992).
Male, David K., "Introduction to the Immune System," Immunology, Third Edition, Mosby-Year Book Europe Ltd., Chpt. 1, pp. 1.1-1.12 (1993).
Matsumoto, Mitsuru et al., "Affinity maturation without germinal centres in lymphotoxin-a-deficient mice," Nature, vol. 382:462-466 (1996).
Matsumoto, Mitsuru et al., "Distinct Roles of Lymphotoxin a and the Type I Tumor Necrosis Factor (TNF) Receptor in the Establishment of Follicular Dendritic Cells from Non-Bone Marrow-derived Cells," J. Exp. Med., vol. 186 (12):1997-2004 (1997).
Matsumoto, Mitsuru et al., "Lymphotoxin-a-deficient and TNF receptor-I-deficient mice define development and functional characteristics of germinal centers," Immunological Reviews, vol. 156:137-144 (1997).
Matsumoto, Mitsuru et al., "Role of Lymphotoxin and the Type I TNF Receptor in the Formation of Germinal Centers," Science, vol. 271:1289-1291 (1996).
Mendlovic, Shlomo et al., "Induction of a systemic lupus erythematosus-like disease in mice by a common human anti-DNA idiotype," Proc. Natl. Acad. Sci. USA, vol. 85:2260-2264 (1988).
Miller, Glenn T. et al., "Specific Interaction of Lymphocyte Function-associated Antigen 3 with CD2 Can Inhibit T Cell Responses," J. Exp. Med., vol. 178:211-222 (1993).
Mohan, Chandra et al., "Interaction Between CD40 and Its Ligand gp39 in the Development of Murine Lupus Nephritis," The Journal of Immunology, vol. 154:1470-1480 (1995).
Morrison, Sherie L. et al., "Chimerica human antibody molecules: Mouse antigen-binding domains with human constant region domains," Proc. Natl. Acad. Sci. USA, vol. 81:6851-6855 (1984).
Morrison, Sherie L., "In Vitro Antibodies: Strategies for Production and Application," Annu. Rev. Immunol., vol. 10:239-265 (1992).

(Continued)

*Primary Examiner* — Prema Mertz
(74) *Attorney, Agent, or Firm* — Nelson Mullins Riley & Scarborough LLP; Debra J. Milasincic, Esq.

(57) ABSTRACT

Compositions and methods comprising "lymphotoxin-β receptor blocking agents" which block lymphotoxin-β receptor signalling and are useful for altering immunological diseases, and particularly antibody mediated immune responses.

29 Claims, 7 Drawing Sheets

OTHER PUBLICATIONS

Nakache, Maurice et al., "The mucosal vascular addressin is a tissue-specific endothelial cell adhesion molecule for circulating lymphocytes," Nature, vol. 337:179-181 (1989).
Neumann, Brigitte et al., "Defective Peyer's Patch Organogenesis in Mice Lacking the 55-kD Receptor for Tumour Necrosis Factor," J. Exp. Med., vol. 184:259-264 (1996).
Pfeffer, Klaus et al., "Mice Deficient for the 55 kd Tumor Necrosis Factor Receptor Are Resistant to Endotoxic Shock, yet Succumb to *L. monocytogenes* Infection," Cell, vol. 73:457-467 (1993).
Picarella, Dominic E. et al., "Insulitis in transgenic mice expressing tumor necrosis factor b (lymphotoxin) in the pancreas," Proc. Natl. Acad. Sci. USA, vol. 89:10036-10040 (1992).
Picker, Louis J. et al., "Physiological and Molecular Mechanisms of Lymphocyte Homing," Annu. Rev. Immunol., vol. 10:561-591 (1992).
Powell, Kenneth L. et al., "The antiviral effects of nitric oxide," Trends in Microbiology, vol. 3(3):81-88 (1995).
Queen, Cary et al., "A humanized antibody that binds to the interleukin 2 receptor," Proc. Natl. Acad. Sci. USA, vol. 86:10029-10033 (1989).
Rennert, Paul D. et al., "Surface Lymphotoxin a/b Complex Is Required for the Development of Peripheral Lymphoid Organs," J. Exp. Med., vol. 184:1999-2006 (1996).
Rennert, P.D. et al., "Normal Development of Lymph Nodes is Disrupted by Soluble LT beta Receptor—Ig Fusion Protein," European Cytokine Network, vol. 7(2):167, No. 17 (1996).
Reuters Health, "What is Systemic Lupus Erythematosus?" retrieved online at http://www.reutershealth.com/wellconnected/doc63.html, pp. 1-32 (2004).
Romagnani, Sergio et al., "Lymphokine Production by Human T Cells in Disease States," Annu. Rev. Immunol., vol. 12:227-257 (1994).
Rothe, Joachim et al., "Mice lacking the tumor necrosis factor receptor 1 are resistant to TNF-mediated toxicity but highly susceptible to infection by *Listeria monocytogenes*," Nature, vol. 364:798-802 (1993).
Schriever, Folke et al., "The Central Role of Follicular Dendritic Cells in Lymphoid Tissues," Advances in Immunology, vol. 51:243-284 (1992).
Selmaj, Krzysztof et al., "Identification of Lymphotoxin and Tumor Necrosis Factor in Multiple Sclerosis Lesions," J. Clin. Invest., vol. 87:949-954 (1991).
Sidman, Kenneth R. et al., "Controlled Release of Macromolecules and Pharmaceuticals from Synthetic Polypeptides Based on Glutamic Acid," Biopolymers, vol. 22:547-556 (1983).
Smith, Craig A. et al., "A Receptor for Tumor Necrosis Factor Defines an Unusual Family of Cellular and Viral Proteins," Science, vol. 248:1019-1023 (1990).
Smith, Craig A. et al., "The TNF Receptor Superfamily of Cellular and Viral Proteins: Activation, Costimulation, and Death," Cell, vol. 76:959-962 (1994).
Smolen, Josef S., "Therapy of systemic lupus erythematosus: a look into the future," Arthritis Res., vol. 4(Suppl. 3): S25-S30 (2002).
Tartaglia, Louis A. et al., "Two TNF receptors," Immunology Today, vol. 13(5):151-153 (1992).
Tew, John G. et al., "Follicular Dendritic Cells as Accessory Cells," Immunological Reviews, vol. 117:185-211 (1990).
Tibbetts, Randal S. et al., "Cardiac Antigen-Specific Autoantibody Production is Associated with Cardiomyopathy in *Trypanosoma cruzi*-Infected Mice," Journal of Immunology, vol. 152:1493-1499 (1994).
Toellner, Kai-Michael et al., "Immunoglobulin Switch Transcript Production In Vivo Related to the Site and Time of Antigen-specific B Cell Activation," J. Exp. Med., vol. 183:2303-2312 (1996).
Traunecker, Andre et al., "Highly efficient neutralization of HIV with recombinant CD4-immunoglobulin molecules," Nature, vol. 339:68-70 (1989).
Trethewey, Pat, "Systemic Lupus Erythematosus," Dimens. Crit. Care Nurs., vol. 23(3):111-115 (2004).

Van Kooten, Cees et al., "CD40-CD40 Ligand: A Multifunctional Receptor-Ligand Pair," Advances in Immunology, vol. 61:1-77 (1996).
Van Vliet, Els et al., "Reticular Fibroblasts in Peripheral Lymphoid Organs Identified by a Monoclonal Antibody," The Journal of Histochemistry and Cytochemistry, vol. 34(7):883-890 (1986).
Ware, C.F. et al., "The Ligands and Receptors of the Lymphotoxin System," Current Topics Microbiol. Immunol., vol. 198:175-218 (1995).
Winter, Greg et al., "Man-made antibodies," Nature, vol. 349:293-299 (1991).
Wu, Qiang et al., "The Requirement of Membrane Lymphotoxin for the Presence of Dendritic Cells in Lymphoid Tissues," J. Exp. Med., vol. 190:629-638 (1999).
International Search Report for Application No. PCT/US97019436, dated May 28, 1998.
Alimzhanov, Marat B. et al., "Abnormal development of secondary lymphoid tissues in lymphotoxin b-deficient mice," Proc. Natl. Acad. Sci. USA, vol. 94:9302-9307 (1997).
Androlewicz, Matthew J. et al., "Lymphotoxin Is Expressed as a Heteromeric Complex with a Distinct 33-kDa Glycoprotein on the Surface of an Activated Human T Cell Hybridoma," The Journal of Biological Chemistry, vol. 267 (4):2542-2547 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," J. Exp. Med., vol. 177:1439-1450 (1993).
Banks, Theresa A. et al., "Lymphotoxin-a-Deficient Mice, Effects on Secondary Lymphoid Organ Development and Humoral Immune Responsiveness," The Journal of Immunology, vol. 155:1685-1693 (1995).
Barnetson, Ross, "Hypersensitivity—Type IV," Essential Immunology, Ivan Roitt, Editor, Chapter 22, pp. 22.1-22.12 (1993).
Bowie, James U. et al., "Deciphering the Message in Protein Sequences: Tolerance to Amino Acid Substitutions," Science, vol. 247:1306-1310 (1990).
Briskin, Michael J. et al., "MAdCAM-1 has homology to immunoglobulin and mucin-like adhesion receptors and to IgA1," Nature, vol. 363:461-464 (1993).
Browning, Jeffrey L. et al., "Characterization of Surface Symphotoxin Forms, Use of Specific Monoclonal Antibodies and Soluble Receptors," The Journal of Immunology, vol. 154:33-46 (1995).
Browning, Jeffrey L. et al., "Lymphotoxin and an Associated 33-kDa Glycoprotein are Expressed on the Surface of an Activated Human T Cell Hybridoma," The Journal of Immunology, vol. 147:1230-1237 (1991).
Browning, Jeffrey L. et al., "Lymphotoxin b, a Novel Member of the TNF Family That Forms a Heteromeric Complex with Lymphotoxin on the Cell Surface," Cell, vol. 72:847-856 (1993).
Browning, Jeffrey L. et al., "Signaling through the Lymphotoxin b Receptor Induces the Death of Some Adenocarcinoma Tumor Lines," J. Exp. Med., vol. 183:867-878 (1996).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Cavert, Winston et al., "Kinetics of Response in Lymphoid Tissues to Antiretroviral Therapy of HIV-1 Infection," Science, vol. 276:960-964 (1997).
Chen, Chyi-Ying A. et al., "AU-rich elements: characterization and importance in mRNA degradation," TIBS, vol. 20:465-470 (1995).
Crowe, Paul D. et al., "A Lymphotoxin-b-Specific Receptor," Science, vol. 264:707-710 (1994).
De Togni, Pietro et al., "Abnormal Development of Peripheral Lymphoid Organ in Mice Deficient in Lymphotoxin," Science, vol. 264:703-707 (1994).
Dijkstra, Christine D. et al., "Marginal zone macrophages identified by a monoclonal antibody: characterization of immuno- and enzyme-histochemical properties and functional capacities," Immunology, vol. 55:23-30 (1985).

Duezguenes, Nejat et al., "Liposome Targeting to HIV-Infected Cells Via Recombinant Soluble CD4 and CD4-IgG (Immunoadhesin)," Journal of Cellular Biochemistry, Poster Selection Q514, p. 77 (1992).

Endres, Robert et al., "Mature Follicular Dendritic Cell Networks Depend on Expression of Lymphotoxin b Receptor by Radioresistant Stromal Cells and of Lymphotoxin b and Tumor Necrosis Factor by B Cells," J. Exp. Med., vol. 189 (1):159-167 (1999).

Eppstein, Deborah A. et al., "Biological activity of liposome-encapsulated murine interferon g is mediated by a cell membrane receptor," Proc. Natl. Acad. Sci. USA, vol. 82:3688-3692 (1985).

Erickson, Sharon L. et al., "Decreased sensitivity to tumour-necrosis factor but normal T-cell development in TNF receptor-2-deficient mice," Nature, vol. 372:560-563 (1994).

Ettinger, Rachel et al., "Disrupted splenic architecture, but normal lymph node development in mice expressing a soluble lymphotoxin-b receptor-IgG1 fusion protein," Proc. Natl. Acad. Sci. USA, vol. 93:13102-13107 (1996).

Fitch, F.W. et al., "Differential Regulation of Murine T Lymphocyte Subsets," Annu. Rev. Immunol., vol. 11:29-48 (1993).

Force, Walker R. et al., "Mouse Lymphotoxin-b Receptor," The Journal of Immunology, vol. 155:5280-5288 (1995).

Foy, Teresa M. et al., "gp39-CD40 Interactions Are Essential for Germinal Center Formation and the Development of B Cell Memory," J. Exp. Med., vol. 180:157-163 (1994).

Fu, Yang-Xin et al., "B Lymphocytes Induce the Formation of Follicular Dendritic Cell Clusters in a Lymphotoxin a-dependent Fashion," J. Exp. Med., vol. 187(7):1009-1018 (1998).

Fu, Yang-Xin et al., "Development and Maturation of Secondary Lymphoid Tissues," Annu. Rev. Immunol., vol. 17:399-433 (1999).

Fu, Yang-Xin et al., "Lymphotoxin-a (LTa) Supports Development of Splenic Follicular Structure That Is Required for IgG Responses," J. Exp. Med., vol. 185(12):2111-2120 (1997).

Fuetterer, Agnes et al., "The Lymphotoxin b Receptor Controls Organogenesis and Affinity Maturation in Peripheral Lymphoid Tissues," Immunity, vol. 9:59-70 (1998).

Gommerman, Jennifer L. et al., "Lymphotoxin/Light, Lymphoid Microenvironments and Autoimmune Disease," Nature, vol. 3:642-655 (2003).

Gonzalez, Mercedes et al., "The Sequential Role of Lymphotoxin and B Cells in the Development of Splenic Follicles," J. Exp. Med., vol. 187(7):997-1007 (1998).

Goodwin, Raymond G. et al., "Molecular and Biological Characterization of a Ligand for CD27 Defines a New Family of Cytokines with Homology to Tumor Necrosis Factor," Cell, vol. 73:447-456 (1993).

Gyoerfy, Zs. et al., "Alteration of the TNF Sensitivity and Membrane Viscosity of Target Cells," European Cytokine Network, vol. 7(2):167, No. 16 (1996).

Han, Shuhua et al., "Cellular Interaction in Germinal Centers, Roles of CD40 Ligand and B7-2 in Established Germinal Centers," The Journal of Immunology, vol. 155:556-567 (1995).

Heath, Sonya et al., "Follicular dendritic cells and human immunodeficiendcy virus infectivity," Nature, vol. 377:740-744 (1995).

Hwang, Karl J. et al., "Hepatic uptake and degradation of unilamellar sphingomyelin/cholesterol liposomes: a kinetic study," Proc. Natl. Acad. Sci. USA, vol. 77(7):4030-4034 (1980).

Kohno, Tadahiko et al., "A second tumor necrosis factor receptor gene product can shed a naturally occurring tumor necrosis factor inhibitor," Proc. Natl. Acad. Sci. USA, vol. 87:8331-8335 (1990).

Kraal, Georg, "Cells in the Marginal Zone of the Spleen," International Review of Cytology, vol. 132:31-74 (1992).

Kraal, Georg et al., "Expression of the Mucosal Vascular Addressin, MAdCAM-1, on Sinus-Lining Cells in the Spleen," American Journal of Pathology, vol. 147(3):763-771 (1995).

Kraal, G. et al., "Lymphocyte migration in the spleen: the effect of macrophage elimination," Immunology, vol. 68:227-232 (1989).

Kraal, G. et al., "Marginal metallophilic cells of the mouse spleen identified by a monoclonal antibody," Immunology, vol. 58:665-669 (1986).

Kratz, Alexander et al., "Chronic Inflammation Caused by Lymphotoxin Is Lymphoid Neogenesis," J. Exp. Med., vol. 183:1461-1472 (1996).

Laman, Jon D. et al., "Functions of CD40 and Its Ligand gp39 (CD40L)," Critical Reviews in Immunology, vol. 16:59-108 (1996).

Lane, Peter et al., "Activated human T cells express a ligand for the human B cell-associated antigen CD40 which participates in T cell-dependent activation of B lymphocytes," Eur. J. Immunol., vol. 22:2573-2578 (1992).

Langer, Robert et al., "Biocompatibility of polymeric delivery systems for macromolecules," Journal of Biomedical Materials Research, vol. 15:267-277 (1981).

Langer, Robert, "Controlled release of macromolecules," Chemtech, vol. 12(2):98-105 (1982).

Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).

Le Hir, Michel et al., "Differentiation of Follicular Dendritic Cells and Full Antibody Responses Require Tumor Necrosis Factor Receptor-1 Signaling," J. Exp. Med., vol. 183:2367-2372 (1996).

Mackay, Fabienne et al., "Lymphotoxin but not tumor necrosis factor functions to maintain splenic architecture and humoral responsiveness in adult mice," Eur. J. Immunol., vol. 27:2033-2042 (1997).

Mackay, Fabienne et al., "Turning off follicular dendritic cells," Nature, vol. 395:26-27 (1998).

```
  1    SQPQAVPPYA  SENQTCRDQE  KEYYEPQHRI  CCSRCPPGTY  VSAKCSRIRD  50
 51    TVCATCAENS  YNEHWNYLTI  CQLCRPCDPV  MGLEEIAPCT  SKRKTQCRCQ  100
101    PGMFCAAWAL  ECTHCELLSD  CPPGTEAELK  DEVGKGNNHC  VPCKAGHFQN  150
151    TSSPSARCQP  HTRCENQGLV  EAAPGTAQSD  TTCKNPLEPL  PPEMSGT     197
```

*Fig. 1*

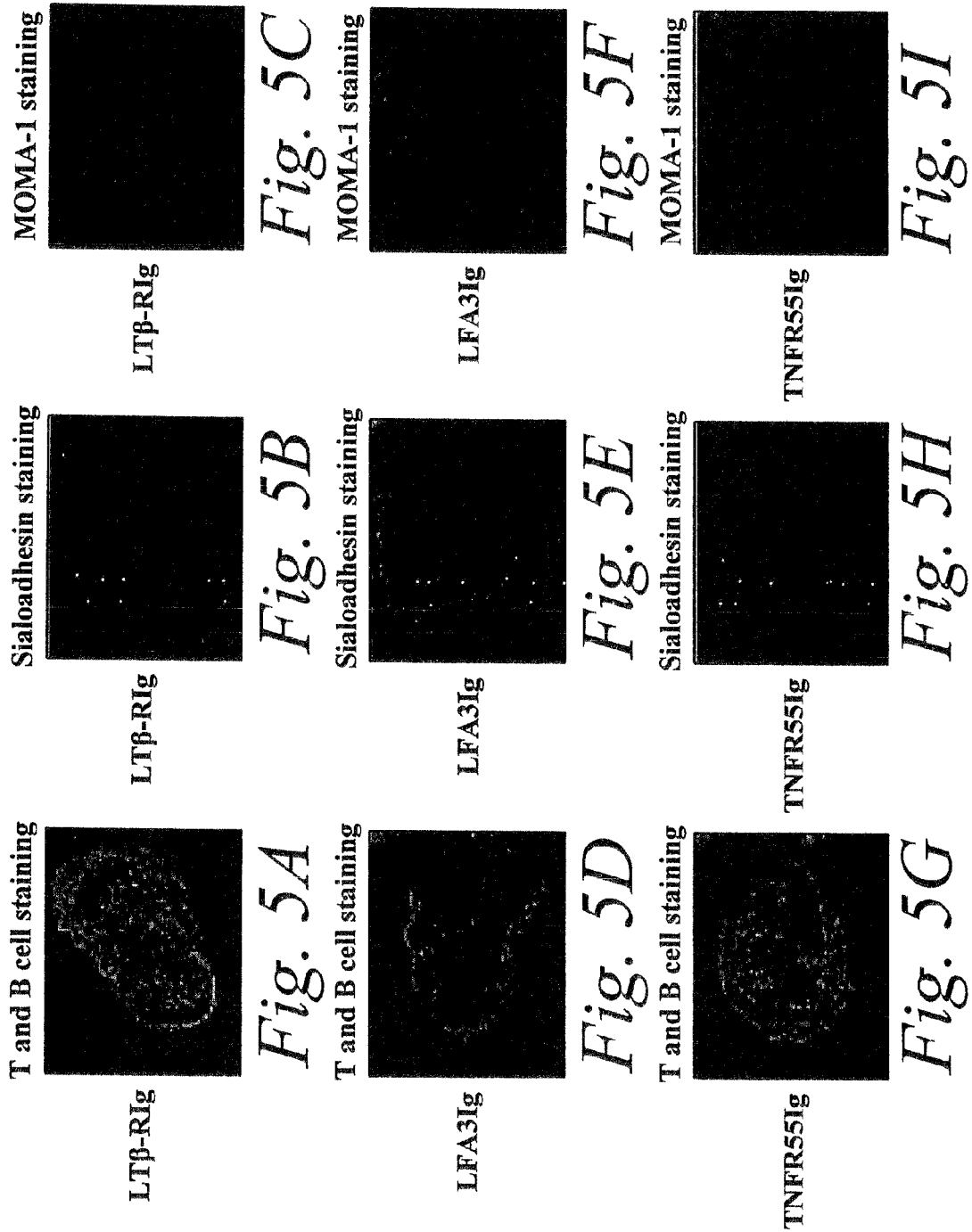

SEQUENCE LISTING

<160> NUMBER OF SEQ ID NOS: 3

<210> SEQ ID NO 1

```
<211> LENGTH: 197
<212> TYPE: PRT
<213> ORGANISM: Homo Sapien

<400> SEQUENCE: 1

Ser Gln Pro Gln Ala Val Pro Pro Tyr Ala Ser Glu Asn Gln Thr Cys
 1               5                  10                  15

Arg Asp Gln Glu Lys Glu Tyr Tyr Glu Pro Gln His Arg Ile Cys Cys
             20                  25                  30

Ser Arg Cys Pro Pro Gly Thr Tyr Val Ser Ala Lys Cys Ser Arg Ile
         35                  40                  45

Arg Asp Thr Val Cys Ala Thr Cys Ala Glu Asn Ser Tyr Asn Glu His
     50                  55                  60

Trp Asn Tyr Leu Thr Ile Cys Gln Leu Cys Arg Pro Cys Asp Pro Val
 65                  70                  75                  80

Met Gly Leu Glu Glu Ile Ala Pro Cys Thr Ser Lys Arg Lys Thr Gln
                 85                  90                  95

Cys Arg Cys Gln Pro Gly Met Phe Cys Ala Ala Trp Ala Leu Glu Cys
            100                 105                 110

Thr His Cys Glu Leu Leu Ser Asp Cys Pro Pro Gly Thr Glu Ala Glu
        115                 120                 125

Leu Lys Asp Glu Val Gly Lys Gly Asn Asn His Cys Val Pro Cys Lys
    130                 135                 140

Ala Gly His Phe Gln Asn Thr Ser Ser Pro Ser Ala Arg Cys Gln Pro
145                 150                 155                 160

His Thr Arg Cys Glu Asn Gln Gly Leu Val Glu Ala Ala Pro Gly Thr
                165                 170                 175

Ala Gln Ser Asp Thr Thr Cys Lys Asn Pro Leu Glu Pro Leu Pro Pro
            180                 185                 190

Glu Met Ser Gly Thr
        195

<210> SEQ ID NO 2
<211> LENGTH: 28
<212> TYPE: DNA
<213> ORGANISM: homo sapien

<400> SEQUENCE: 2
aactgcagcg gccgccatgc gcctgccc                                          28

<210> SEQ ID NO 3
<211> LENGTH: 33
<212> TYPE: DNA
<213> ORGANISM: homo sapien

<400> SEQUENCE: 3
gactttgtcg accattgctc ctggctctgg ggg                                    33
```

SOLUBLE LYMPHOTOXIN-BETA RECEPTORS AND ANTI-LYMPHOTOXIN RECEPTOR AND LIGAND ANTIBODIES AS THERAPEUTIC AGENTS FOR THE TREATMENT OF IMMUNOLOGICAL DISEASES

RELATED APPLICATIONS

This application is a continuation of U.S. Ser. No. 11/891,847 (filed Aug. 13, 2007), which is a continuation of U.S. Ser. No. 09/299,139 (filed Apr. 23, 1999) issued as U.S. Pat. No. 7,255,854, which is a continuation of PCT/US97/19436 (filed Oct. 24, 1997) under 35 U.S.C. §111(a), which claims priority to U.S. Provisional Patent Application Ser. No. 60/029,060 (filed Oct. 25, 1996), the contents of which are hereby incorporated herein.

TECHNICAL FIELD OF THE INVENTION

This invention relates to compositions and methods comprising "lymphotoxin-β receptor blocking agents" which block lymphotoxin-β receptor signaling. Lymphotoxin-β receptor blocking agents are useful for treating immunological diseases, more specifically for inhibiting antibody mediated immune responses, regulating the expression of addressins and cell trafficking, and influencing the differentiation of follicular dendritic cells. This invention relates to soluble forms of the lymphotoxin-β receptor extracellular domain, and antibodies directed against either the lymphotoxin-β receptor or its ligand, surface lymphotoxin, that act as lymphotoxin-β receptor blocking agents.

BACKGROUND OF THE INVENTION

There are two arms of acquired immunity, which, while able to collaborate to achieve the common goal of eliminating antigen, are mediated by distinct participants of the immune system with different effects. One arm of acquired immune response, humoral immunity, is mediated primarily by B cells and circulating antibodies. The other arm, referred to as cellular or cell-mediated immunity, is mediated by T cells that synthesize and elaborate cytokines which affect other cells.

Activation and differentiation of B cells in response to most antigens requires that (1) B cells receive an antigen signal via their antigen specific receptor, membrane Ig, and (2) B cells receive contact dependent and independent signals from activated T cells. The contact dependent costimulatory signal results from ligation of the CD40 receptor on B cells to the CD40 ligand expressed on activated T helper cells.

(Laman et al., *Crit. Rev. Immunol.*, 16, pp. 59-108 (1996); Van Kooten and Banchereau, *Adv. Immunol.*, 61, pp. 1-77 (1996)). Contact independent signaling is mediated by cytokines synthesized and elaborated by activated T cells. Together these contact dependent and independent signals drive B cells to differentiate to either (1) memory B cells poised to mediate a more rapid response upon secondary exposure to antigen, or (2) antibody secreting plasma cells. Plasma cells, which are the terminal differentiation stage of B cells, synthesize and secrete antibodies.

T helper cells ("Th") play several significant roles in the immune system. Cytokines elaborated by Th cells at the onset of an immune challenge have been shown to affect which immune effector pathways are subsequently activated. Th cells are activated by the interaction of their antigen specific receptor with antigen-presenting cells (APCs) displaying on their surfaces peptide fragments of processed foreign antigen in association with MHC class II molecules. Activated Th cells, in turn, secrete cytokines (lymphokines) which activate the appropriate immune effector mechanisms.

Th cells can be divided into three subgroups Th0, Th1 and Th2, based upon their cytokine secretion patterns. (Fitch et al., *Ann. Rev. Immunol.*, 11, pp. 29-48 (1993)). In mice, non-stimulated "naive" T helper cells produce IL-2. Short term stimulation of Th cells leads to Th0 precursor cells, which produce a wide range of cytokines including IFN-α, IL-2, IL-4, IL-5 and IL-10. Chronically-stimulated Th0 cells can differentiate into either Th1 or Th2 cell types, whereupon the cytokine expression pattern changes. Certain cytokines, for example IL-3, GM-CSF and TNF, are released by both Th1 and Th2 cells. Other cytokines are made exclusively by only one Th cell subgroup. (Romagnani et al., *Ann. Rev. Immunol.*, 12, pp. 227-57 (1994)). Th1 cells produce LTα IL-2 and IFN-γ which activate macrophages and inflammatory responses associated with cellular immunity and resistance to intracellular infections.

Th2 cells produce the cytokines IL-4, IL-5, IL-6 and IL-10 which increase eosinophil and mast cell production and promote the full expansion and maturation of B cells. (Howard et al., "T cell-derived cytokines and their receptors", *Fundamental Immunology*, 3d ed., Raven Press, New York (1993)). Th2 cells also participate in generating B cell memory, somatic mutation and thus affinity maturation, and in regulating de novo immunoglobulin isotype switching. For example, the Th2 cytokine IL-4 switches activated B cells to the IgG1 isotype while suppressing other isotypes. IL-4 also stimulates the overproduction of IgE in type I hypersensitivity reactions. The Th2 cytokine IL-5 induces the IgA isotype important in mucosal immunity.

The secondary lymphoid tissues, such as the lymph nodes (LN), spleen and mucosal lymphoid tissues, are highly efficient in trapping and concentrating foreign substances, and are the main sites of antigen driven activation and differentiation of T and B lymphocytes. These processes are dependent upon the diversity and organization of cells in these tissues, providing a framework for many aspects of humoral immune responses, such as T/B cell interactions, germinal center (GC) formation, affinity maturation, immunoglobulin class switching and cell trafficking. (Klein, J., Immunology, John Wiley and sons, (1982)). The molecular mechanisms responsible for the development, structural maintenance and function of peripheral lymphoid tissues are not fully understood.

Although the general structure of the secondary lymphoid tissues differs markedly and shows variations between species of mammalia, the fine structure of these secondary lymphoid tissues shares certain features, such as, for example: (1) antigen accessibility, (2) structural features ensuring continued contact of antigen with lymphocytes, (3) T cell rich areas surrounded by B cells, (4) B cell rich follicles, (5) marginal zone type sites, (6) specialized endothelial cells, and (7) antibody production sites, as discussed in further detail below.

The secondary lymphoid tissues are accessible to antigen in the system. For example, antigen accesses the spleen via the sinusoidal blood supply, the LN via the afferent lymphatic vessels, and is transported across specialized epithelium into the mucosal lymphoid tissue.

The secondary lymphoid tissues in various species also share certain structural features such as follicular dendritic cells (FDC) and interdigitating cells (IDC), which ensure the continued presence of antigen in the lymphocyte rich areas of the tissues.

Another common feature is the presence of T cell rich areas surrounded by B cells. T cell rich areas include, for example, the periarteriolar lymphoid sheaths in the white pulp of the spleen, and the paracortical region of LN, which contain large numbers of recirculating T cells and IDC, which in turn function as accessory cells for T and B cells.

Additionally, lymphoid tissues typically have B cell rich primary and secondary follicles in the white pulp of the spleen, and in the cortex of the LN. Secondary follicles in such lymphoid tissues are also called germinal centers (GC) and have a dense FDC network to capture and present antigens. Marginal—zone type areas are also noted as defined histologic areas in the murine spleen and more diffuse sites in human secondary lymphoid organs. These areas are comprised primarily of marginal zone macrophages (MZM), metallophilic macrophages (MM), marginal zone B cells and reticular cells, but may also include T cells and dendritic cells. (Kraal, Int. Rev. Cytol. 132, pp. 31-74 (1992)). The opening of the arterial blood stream into the marginal zone areas gives antigens direct access to these cells and promotes cellular reactions to antigens at this site. (Kraal, *Int. Rev. Cytol.* 132, pp. 31-74 (1992)). The presence of MZM are also required for optimal trafficking of B cells in the splenic white pulp. (Kraal, 1992; Kraal, et al, *Immunology,* 68, pp. 227-232 (1989)).

Typically, blood lymphocytes enter the secondary lymphoid tissues by crossing specialized endothelium, for example the endothelial lining of the venules of LN (high endothelial venules—HEV) and the endothelial lining of splenic blood sinusoids in the marginal zone—like structures. This endothelium expresses adhesion molecules and addresssins which function in the trafficking of cells to secondary lymphoid tissues. For example, peripheral LN addressins (PNAd) are distinct from the mucosal LN addressin, MAdCAM-1, which is involved in trafficking of lymphocytes to mucosal lymphoid tissues, including tissues such as the esenteric LN, Peyer's patches and lamina propria.

Not all addressins are clearly defined, for example, the addressin for lymphocyte homing to spleen remains undefined. The physiological roles of these addressins include enhancing recruitment of appropriate sets of antigen specific lymphocytes into an immune response, and subsequent dissemination of the immune response throughout the body.

Finally, the plasma cells, which are the antibody producing plasma cells, are detected at different locations from where the progenitor B cells are activated by antigen. For example, antibody produced by plasma cells in splenic red pulp mainly results from B cell activation in T cell zones, and plasma cells in the medulla of LN are derived from B cells activated in T cell zones of the same node. Similarly, antibody produced by plasma cells in bone marrow are derivatives of B cells activated in spleen and lymph node, and plasma cells in the lamina propria of gut mainly derive from B cells activated in mesenteric LN or gut associated lymphoid tissue.

See e.g., ICM MacLennan, "The Structure and Function of Secondary Lymphoid Tissues" in *Clinical Aspects of Immunology* 5th edition, eds. P. J. Lachman, Sir D. K. Peters, F. S. Rosen, M. J. Walport, Blackwell Scientific Publications pp 13-30 (1993).

In general, the cellular/histologic events underlying a humoral immune response to T dependent antigens are as follows (Toellner, et al., *J. Exp. Med.,* 183, pp. 2303-2312 (1996)):

In the Inductive phase, naive B and T cells are activated and recruited into the immune response in the days immediately after antigen enters the body. In the spleen, for example, within 12 hours of immunization for a secondary response, memory B cells encounter blood-borne antigen in the marginal zone and leave the marginal zone to go to the T cell zones. B cells can be detected in the T cell zones within 24 hours. Immunoglobulin switch transcripts can be detected within 12 hours of secondary antigen exposure, thus indicating that the T-B cell interaction has already occurred. The B cells then migrate to the exit zones and red pulp where they proliferate to form foci of B cell blasts and differentiate into plasma cells. The B cells also continue to proliferate in the IDC rich T cell zone. Within 4 days after immunization, and after proliferation in the GC, B memory cell production will start. In a primary response, well developed GC are apparent by day 10 and reach peak size by day 14 post-immunization T cell proliferation in the T cell zones becomes evident 48-72 hours and peaks on day 7 after immunization. This T cell proliferation contributes to T cell dependent B cell activation. Proliferative levels in the T cell zone decrease as GC forms. T cell proliferation also occurs in the GC where centrocytes (B cells) in the dark zone pick up antigen from IDC, and present antigen to T cells in light zone.

T cell dependent antigen can activate marginal zone B cells, newly produced naive B cells and recirculating lymphocytes attracted to and retained in secondary lymphoid organs by addressins and adhesion molecules. Naive B cells show the same kinetics for going to T cell zone, etc. as do the activated B cells.

Established Phase of T Cell Dependent Responses

The established phase of T cell dependent responses is maintained by the continued activation of memory B cells in the follicles of secondary lymphoid organs. There is very little recruiting of naive B cells at this stage, and the response is primarily driven by antigen retained on FDC. GC are required for optimal memory generation, isotype switching, somatic mutation and thus affinity maturation of immunoglobulin.

The mounting of such lymphocyte responses results in the production of antibodies able to circulate throughout the body by various routes, for example, antibodies leave the spleen via the blood, and exit LN via the efferent lymphatics. The antibodies thus encounter and directly bind to the invading pathogen. This recognition event sets off a cascade of immune effector mechanisms, including activation of the complement cascade and cellular reactions to mediate protection of the host from the pathogen.

Antibodies also play a role in some pathologic responses such as hypersensitivity responses—inappropriate or disproportionate immune responses evoked upon contact with a previously encountered antigen. There are four recognized types of hypersensitivity.

Type I "immediate hypersensitivity" involves allergen-induced Th2 cell activation and Th2 cytokine release. The Th2 cytokine IL-4 stimulates B cells to undergo isotype switching to produce IgE, which in turn activates mast cells to produce acute inflammatory reactions such as those which lead to eczema, asthma and rhinitis.

Types II and III hypersensitivity are caused by IgG and IgM antibodies directed against cell surface antigens or specific tissue antigens (Type II) or soluble serum antigens to form circulating immune complexes (Type III).

Type IV "delayed type" hypersensitivity (DTH) is a Th1 cell mediated response and can be transferred between mice by transferring Th1 cells, but not by transferring serum alone. This feature distinguishes Type IV DTH from the other three types of hypersensitivity, which require humoral immune responses caused primarily by antibodies which can be transferred in cell-free serum. (Roitt et al., *Immunology, pp.* 19.1-22.12 (Mosby-Year Book Europe Ltd., 3d ed. 1993))

Pathological humoral immune responses are associated with a number of organ-specific and systemic autoimmune conditions such as Systemic Lupus Erythematosus, Wegener's Granulomatosis, Polyarteritis Nodosa (PAN), Rapidly Progressive Crescentic Glomerulonephritis and Idiopathic Thrombocytopenia Purpura, as well as chronic inflammatory diseases such as the Graves' and Chagas' disease. Humoral immune responses may also contribute to grafted tissue and transplanted organ rejection.

The treatment of these various immunological conditions to date has generally employed immunomodulatory and immunosuppressive agents. Three general immunosuppressive agents currently used are steroids, cyclophosphamide and azathioprine.

Steroids are pleiotropic anti-inflammatory agents which suppress activated macrophages and inhibit the activity of antigen presenting cells in ways which reverse many pathologic T cell effects. Cyclophosphamide, an alkylating agent, mediates cell death by inhibiting DNA replication and repair. Azathioprine is an anti-proliferative agent which inhibits DNA synthesis. These non-specific immunosuppressive agents are generally required in high doses which increase their toxicity (e.g. nephro- and hepatotoxicity) and cause adverse side effects. They are thus unsuitable for long term therapies.

Thus, there is an unmet need for additional agents and therapies which overcome the problems caused by conventional treatments.

SUMMARY OF THE INVENTION

The present invention solves the problems referred to above by providing pharmaceutical compositions and methods for treating immunological diseases by inhibiting lymphotoxin-β receptor (LT-β-R) signaling using lymphotoxin-β receptor blocking agents. More particularly, the compositions and methods comprising LT-β-R blocking agents are useful for inhibiting antibody mediated immune responses, for regulating addressin expression levels and cell trafficking, for influencing the differentiation of follicular dendritic cells, and for altering the structural organization of secondary lymphoid tissues and similar lymphoid structures arising in pathologic conditions such as, for example, systemic lupus erythematosis and idiopathic thrombocytopenia purpura. Additionally, in certain embodiments the claimed invention is useful for altering the association between immune complexes and B cells. More specifically, the methods of the invention can prevent the presentation or deposition of antigens on cells, or alternatively, to essentially dissolve or erase the antigens already present on cells.

In alternative embodiments, the LT-β-R blocking agent is selected from the group consisting of soluble lymphotoxin-β-R, an antibody directed against LT-β-R, and an antibody directed agains surface LT ligand.

In one embodiment, soluble forms of the lymphotoxin-β receptor extracellular domain that act as LT-β-R blocking agents are provided. The preferred compositions and methods of this embodiment comprise a recombinant lymphotoxin-β receptor fusion protein that has the LT-β-R extracellular ligand binding domain fused to an immunoglobulin constant heavy chain domain. More preferably, the LT-β-R ligand binding domain is fused to a human IgG Fc domain.

In another embodiment of this invention, antibodies that act as LT-β-R blocking agents are provided. Preferred compositions and methods of this embodiment comprise one or more antibodies directed against the lymphotoxin-β receptor. More preferably, the antibody is a monoclonal antibody. Other preferred compositions and methods of this embodiment comprise one or more antibodies directed against surface lymphotoxin. More preferably, the antibody is a monoclonal antibody directed against lymphotoxin-β. Preferred antibodies include the anti-human LT-β-R mAb BDA8, and anti-human LT-β mAb B9.

In yet other emboidments, the claimed invention relates to methods of altering the humoral immune response in an animal by administering a pharmaceutical composition which has a therapeutically effective amount of a LT-β-R blocking agent. In certain other embodiments, the pharmaceutical composition is administered in an amount sufficient to coat LT-β-R positive cells for about 1 to about 14 days. The pharmaceutical composition may in certain embodiments further comprise a pharmaceutically acceptable carrier or adjuvant.

In other embodiments, the claimed methods inhibit LT-β-R signaling without inhibiting TNF-R signaling, using the LT-β-R blocking agents described above. Methods of treating, preventing, or eliminating the human immunodeficiency virus in a mammal are also encompasses in the claimed invention, comprising administration of blocking agents of LT-β-R either alone, or in conjunction with pharmaceutical carriers, adjuvants, or other drugs known to those skilled in the art to be useful in the treatment or amelioration of the symptoms of HIV or AIDS.

Additionally, the present invention relates to methods of treatment in the transplantation field, i.e. graft rejection. Specifically, certain embodiments relate to the coadministration of a blocking agent of the CD40 pathway and a blocking agent of the LT pathway.

BRIEF DESCRIPTION OF THE DRAWINGS

FIG. 1 is a sequence of the extracellular portion of the human LTβ receptor which encodes the ligand binding domain.

FIG. 5 is an immunohistochemical analysis of Lymphocyte positioning and expression of macrophage markers in mesenteric LN of mice treated (as for FIG. 4) in utero and continuously post-birth with LTβ-R-Ig.

DETAILED DESCRIPTION OF THE INVENTION

Figure 2:
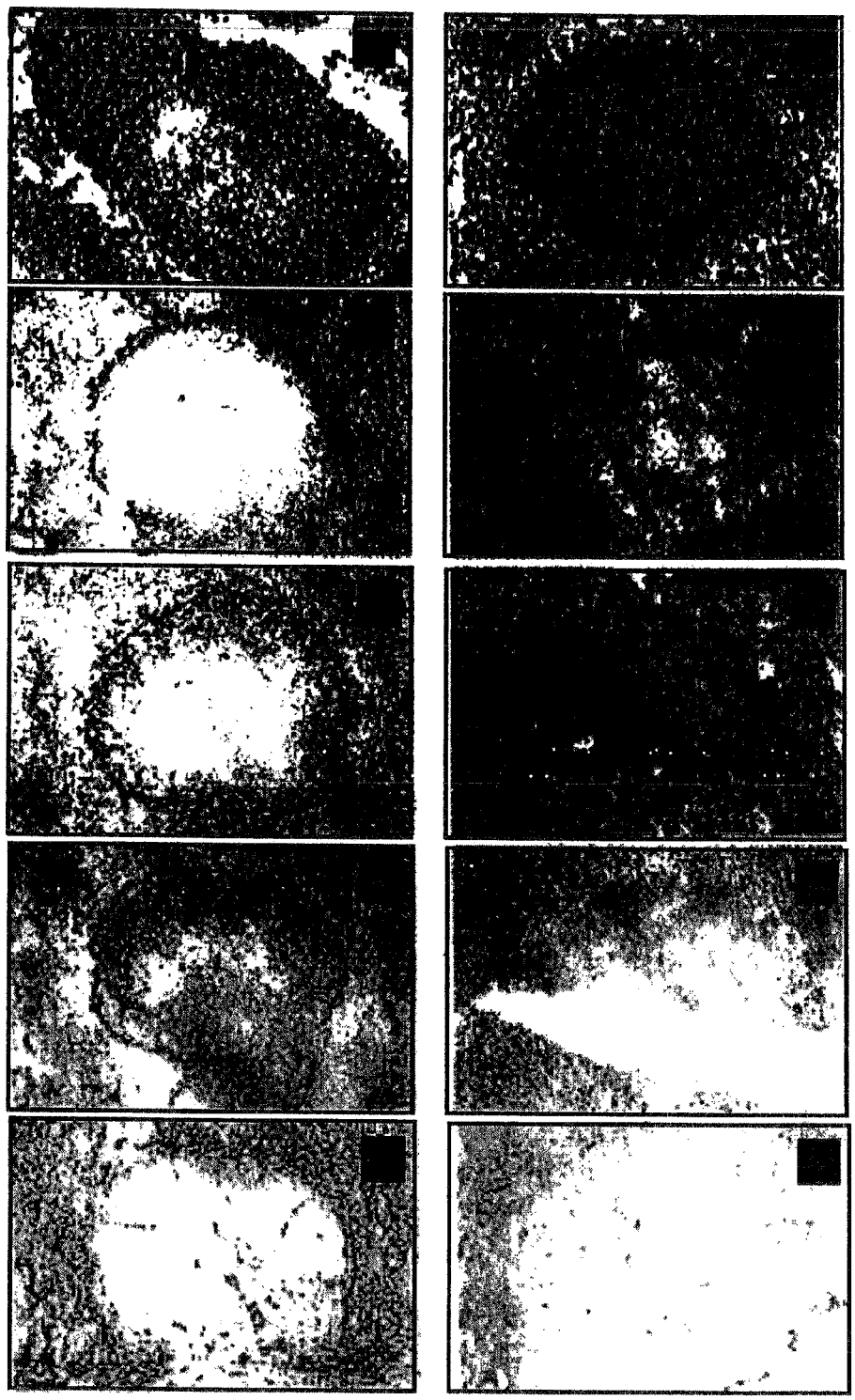
FIG. 2 is an immunohistochemical analysis of the spleen of mice which received multiple injections of LTβ-R-Ig or LFA-3-Ig fusion proteins, and antigen.

In order that the invention herein described may be fully understood, the following detailed description is set forth.

The terms "immunoglobulin response" or "humoral response" as used herein refer to the immunological response of an animal to a foreign antigen whereby the animal produces antibodies to the foreign antigen. The Th2 class of T helper cells are important to the efficient production of high affinity antibodies.

The term "germinal center" as used herein refers to a secondary B cell follicle which forms after antigen immunization. The appearance of this histologic site correlates with optimal memory generation, isotype switching, somatic hypermutation and thus the affinity maturation of an antibody response.

The terms "marginal zone" or "marginal—zone type area" refer to histologically described compartments of the secondary lymphoid tissues comprised primarily of marginal zone macrophages (MZM), metallophilic macrophages (MM), marginal zone B cells and reticular cells, and also T cells and dendritic cells. The arterial blood stream opens into the marginal sinuses thus giving antigens direct access to these cells and promoting cellular reactions to antigens at this site.

The term "addressin" as used herein refers to a molecule involved in the homing of lymphocytes to secondary lymphoid organs. Such molecules are expressed on endothelial cells, specifically the high endothelial venules in the lymph nodes. The splenic addressin is undefined. MAdCAM-1 is a mucosal addressin; PNAd is a peripheral addressin.

The term "T helper (Th) cells" as used herein, refers to a functional subclass of T cells which help to generate cytotoxic T cells and which cooperate with B cells to stimulate antibody production. Helper T cells recognize antigen in association with class II MHC molecules and provide contact dependent and contact independent (cytokine) signals to effector cells.

The term "cytokine", as used herein, refers to a molecule which mediates signaling between cells. A "lymphokine" is a cytokine released by lymphocytes.

The term "Th1" refers to a subclass of T helper cells that produce LTα, interferon-γ and IL-2 (and other cytokines) and which elicit inflammatory reactions associated with a cellular, i.e. non-immunoglobulin, response to a challenge.

The term "Th2" refers to a subclass of T helper cells that produces cytokines, such as IL-4, IL-5, IL-6 and IL-10, which are associated with an immunoglobulin (humoral) response to an immune challenge.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-LTβ receptor antibody" refers to any antibody that specifically binds to at least one epitope of the LTβ receptor.

The term "anti-LT antibody" refers to any antibody that specifically binds to at least one epitope of LTα, LTβ or a LTα/β complex.

The term "LTβ-R signaling" refers to molecular reactions associated with the LTβ-R pathway and subsequent molecular reactions which result therefrom.

The term "LTβ-R blocking agent" refers to an agent that can diminish ligand binding to LTβ-R, cell surface LTβ-R clustering or LTβ-R signaling, or that can influence how the LTβ-R signal is interpreted within the cell.

A LTβ-R blocking agent that acts at the step of ligand-receptor binding can inhibit LT ligand binding to the LTβ-R by at least 20%. Examples of LTβ-R blocking agents include soluble LTβ-R-Fc molecules, and anti-LT α, anti-LTβ, anti-LT α/β and anti-LTβ-R Abs. Preferably, the antibodies do not cross-react with the secreted form of LT α.

The term "LTβ-R biological activity" refers to: 1) the ability of the LTβ-R molecule or derivative to compete for soluble or surface LT ligand binding with soluble or surface LTβ-R molecules; or 2) native LTβ activity such as the ability to stimulate an immune regulatory response or cytotoxic activity.

The term "LT ligand" refers to a LT α/β heteromeric complex or derivative thereof that can specifically bind to the LTβ receptor.

The term "LTβ-R ligand binding domain" refers to the portion or portions of the LTβ-R that are involved in specific recognition of and interaction with a LT ligand.

The terms "surface LT" and "surface LT complex" refer to a complex comprising LT α and membrane-bound LTβ subunits—including mutant, altered and chimeric forms of one or more of the subunits—which is displayed on the cell surface.

"Surface LT ligand" refers to a surface LT complex or derivative thereof that can specifically bind to the LTβ receptor.

The term "subject" refers to an animal, or to one or more cells derived from an animal. Preferably, the animal is a mammal. Cells may be in any form, including but not limited to cells retained in tissue, cell clusters, immortalized, transfected or transformed cells, and cells derived from an animal that has been physically or phenotypically altered.

Lymphotoxin β: A Member of the TNF Family

Tumor Necrosis Factor (TNF)-related cytokines have emerged as a large family of pleiotropic mediators of host defense and immune regulation. Members of this family exist in membrane-bound forms which act locally through cell-cell contact, or as secreted proteins which can act on distant targets. A parallel family of TNF-related receptors reacts with these cytokines and triggers a variety of pathways including cell death, cell proliferation, tissue differentiation and proinflammatory responses.

TNF, lymphotoxin α (LTα, also called TNFβ) and lymphotoxin β (LTβ) are members of the TNF family of ligands, which also includes the ligands to the Fas, CD27, CD30, CD40, OX-40 and 4-IBB receptors. (Smith et al., *Cell*, 76, pp. 959-62 (1994)). Signaling by several members of the TNF family—including TNF, LTα, LTβ and Fas—can induce tumor cell death by necrosis or apoptosis (programmed cell death). In non-tumorigenic cells, TNF and many of the TNF family ligand-receptor interactions influence immune system development and responses to various immune challenges.

Most membrane-associated LTα/β complexes ("surface LT") have a LTα1/β2 stoichiometry. (Browning et al., *Cell*, 72, pp. 847-56 (1993); Browning et al., *J. Immunol.*, 154, pp. 33-46 (1995)). Surface LT ligands do not bind TNF-R with high affinity and do not activate TNF-R signaling. The LTβ receptor (LTβ-R), does however bind these surface lymphotoxin complexes with high affinity (Crowe et al., *Science*, 264, pp. 707-10 (1994)).

LTβ-R signaling, like TNF-R signaling, has anti-proliferative effects and can be cytotoxic to tumor cells. In applicants' co-pending U.S. application Ser. No. 08/378,968, compositions and methods for selectively stimulating LTβ-R using LTβ-R activating agents are disclosed. LTβ-R activating agents are useful for inhibiting tumor cell growth without co-activating TNF-R-induced proinflammatory or immunoregulatory pathways.

Recent gene targeting studies suggest a role for LTα/β in the development of secondary lymphoid organs. (Banks et al., *J. Immunol.*, 155, pp. 1685-1693 (1995); De Togni et al., *Science*, 264, pp. 703-706 (1994)).

Indeed, LTα-deficient mice lack lymph nodes (LN) and Peyer's patches (PP). Moreover, their spleens have disrupted architecture and the expression of functional markers on cells of the splenic marginal zone is altered. (Banks et al., 1995; De Togni et al., *Science*, 264, pp. 703-706 (1994), Matsumoto et al., *Science*, 271, pp. 1289-1291 (1996)). None of these characteristics have been described for either of the TNF receptor knock out mice. (Erickson et al., *Nature,* 372, pp. 560-563 (1994); Pfeffer et al. *Cell,* 73, pp. 457-467 (1993); Rothe et al., *Nature,* 364, pp. 798-802 (1993). Applicants have recently defined a role for membrane LTα/β complexes in secondary lymphoid organ development by showing that the progeny of mice which had been injected during gestation with a soluble form of mouse LTβ-R fused to the human IgG1 Fc portion (LTβ-R-Ig) lacked most lymph nodes and showed disrupted splenic architecture. (Rennert et al, 1996, "Surface Lymphotoxin alpha/beta complex is required for the development of peripheral lymphoid organs." *J. Exp Med,* 184: 1999-2006). In another study, mice transgenic for a similar LTβ-R-Ig construct which starts to be expressed three days after birth, were shown to have LN. However, their splenic architecture was disrupted and several markers of splenic marginal zone cells were not expressed (Ettinger et al., "Disrupted splenic architecture, but normal lymph node development in mice expressing a soluble LTβ-R/IgG1 fusion protein"., *Proc. Natl. Acac. Sci. U.S.A.* 93: 13102-7). Together these data indicate there is a temporal requirement for membrane LT functions to mediate effects on the development of secondary lymphoid organs, but not for effects on splenic architecture.

The TNF system may also function in development of the spleen. Splenic marginal zone cells of TNF-deficient mice do not express macrophage markers or MAdCAM-1 (Alexopoulou et al., 60*th Int. TNF Congress, Eur. Cytokine Network,* pp. 228 (1996); Pasparakis et al., 60*th Int. TNF Congress, Eur. Cytokine Network,* pp. 239 (1996)). TNF-R55-deficient mice also lack MAdCAM-1 (but not MOMA-1) staining in the splenic marginal zone. (Neumann et al., *J. Exp. Med.,* 184, pp. 259-264 (1996), Matsumoto et al., *Science,* 271, pp. 1289-1291 (1996)). The expression of these markers as seen in the spleen of TNF-R75-deficient mice appears normal. (Matsumoto et al., *Science,* 271, pp. 1289-1291 (1996)).

Lymphoid-like tissues do not only arise as a part of developmental processes but also appear under some pathological circumstances such as chronic inflammation, a process recently termed neolymphoorganogenesis. (Picker and Butcher, *Annu. Rev. Immunol.,* 10, pp. 561-591 (1992), Kratz, et al., *J. Exp. Med.,* 183, pp. 1461-1471 (1996)). Such processes are apparently influenced by TNF family members. Mice transgenic for the LTα gene driven by the rat insulin promoter (RIP-LT) developed LT-induced chronic inflammatory lesions with characteristics of organized lymphoid tissues. (Kratz, et al., *J. Exp. Med.,* 1183, pp. 1461-1471 (1996); Picarella et al., *Proc. Natl. Acad. Sci.,* 89, pp. 10036-10040 (1992)).

The evaluation of LT function during a T cell—dependent immune response, using LTα-deficient mice, showed the necessity of LT for GC formation, possibly for maintaining an organized follicular dendritic cell (FDCs) structure, and for humoral responses. (Banks et al., *J. Immunol.,* 155, pp. 1685-1693 (1995); Matsumoto et al., *Science,* 271, pp. 1289-1291 (1996); Matsumoto et al., *Nature,* 382, pp. 462-466 (1996)).

TNF-R55-deficient mice also lack FDCs, fail to develop GC and fail to develop an optimal antibody response to sheep red blood cells (SRBC). This suggests that TNF-R55 might be triggered by soluble LT or TNF signals for most of these responses (Le Hir et al., *J. Exp. Med.,* 183, pp. 2367-2372 (1996), Alexopoulou et al., 60*th Int. TNF Congress, Eur. Cytokine Network,* pp. 228 (1996); Pasparakis et al., 60*th Int. TNF Congress, Eur. Cytokine Network,* pp. 239 (1996)). A functional role for the surface LT/LTβ-R pathway in the humoral immune responses has to date been undefined.

The LTβ receptor, a member of the TNF family of receptors, specifically binds to surface LT ligands. LTβ-R binds LT heteromeric complexes (predominantly LTα1/β2 and LTα2/β1) but does not bind TNF or LTa (Crowe et al., *Science,* 264, pp. 707-10 (1994)). LTβ-R mRNAs are found in the human spleen, thymus and in general organs with immune system involvement. Although studies on LTβ-R expression are in their early stages, LTβ-R expression patterns appear to be similar to those reported for TNF-R55 except that LTβ-R is lacking on peripheral blood T and B cells and T and B cell lines.

Cell surface lymphotoxin (LT) complexes have been characterized in CD4$^+$T cell hybridoma cells (II-23. D7) which express high levels of LT. (Browning et al., *J. Immunol.,* 147, pp. 1230-37 (1991); Androlewicz et al., *J. Biol. Chem.,* 267, pp. 2542-47 (1992), both of which are herein incorporated by reference). The expression and biological roles of LTβ-R, LT subunits and surface LT complexes have been reviewed by C. F. Ware et al. "The ligands and receptors of the lymphotoxin system", in *Pathways for Cytolysis, Current Topics Microbiol. Immunol.,* Springer-Verlag, pp. 175-218 (1995) specifically incorported by reference herein.

LTα expression is induced and LTα secreted primarily by activated T and B lymphocytes and natural killer (NK) cells. Among the T helper cells, LTa appears to be produced by Th1 but not Th2 cells. LTα has also been detected in melanocytes. Microglia and T cells in lesions of multiple sclerosis patients can also be stained with anti-LTa antisera (Selmaj et al., *J. Clin. Invest.,* 87, pp. 949-954 (1991)).

Lymphotoxin β (also called p33) is expressed on the surface of human and mouse T lymphocytes, T cell lines, B cell lines and lymphokine-activated killer (LAK) cells. LTβ is the subject of applicants' co-pending international applications PCT/US91/04588, published Jan. 9, 1992 as WO 92/00329; and PCT/US93/11669, published Jun. 23, 1994 as WO 94/13808, which are herein incorporated by reference.

Surface LT complexes are primarily expressed by activated T (helper, Th1, and killer cells) and B lymphocytes and natural killer (NK) cells as defined by FACS analysis or immunohistology using anti-LTa antibodies or soluble LTβ-R-Ig fusion proteins. In applicants copending U.S. application Ser. No. 08/505,606, filed Jul. 21, 1995, compositions and methods for using soluble LTβ receptors and anti-LTβ receptor and ligand specific antibodies as therapeutics for the treatment of immunological diseases mediated by Th1 cells are disclosed. Surface LT has also been described on human cytotoxic T lymphocyte (CTL) clones, activated peripheral mononuclear lymphocytes (PML), IL-2-activated peripheral blood lymphocytes (LAK cells), pokeweed mitogen-activated or anti-CD40-activated peripheral B lymphocytes (PBL) and various lymphoid tumors of T and B cell lineage. Engagement of alloantigen-bearing target cells specifically induces surface LT expression by CD8$^+$and CD4$^+$CTL clones.

Applicants have described herein several immunological functions for surface LT, and show the effects of LTα/β binding reagents on the generation and character of immunoglobulin responses, maintenance of the cellular organization of secondary lymphoid tissues including effects on the differentiation state of follicular dendritic cells and germinal center formation, and addressin expression levels which influence cell trafficking. Thus applicants define therapeutic applications for surface LTα/β and LTβ receptor binding agents.

Until the present invention, however, the impact of LT-β-R signaling on humoral, or immunogenic, responses has not been fully understood. The inventors have, for the first time, discovered that blocking the LT pathway, either LT-β or LT-β-R can alter the humoral immune response in an animal. Thus, the claimed invention in a broad embodiment relates to methods of altering the humoral immune response in an animal comprising the steps of administering a pharmaceutical composition which comprises a therapeutically effective amount of a blocking agent of the LT pathway, specifically preferred, LT-β-R blockers.

Any blocking agent can be used in the invention, and one skilled in the art can easily determine agents which block the LT-β-R. For example, such blocking agents may include small molecule inhibitors of the receptor, soluble lymphotoxin-β-Receptor, antibodies directed against the LT-β-R, and antibodies directed against the surface LT ligand. In preferred embodiments, the blocking agents comprise a soluble LT-β-R having a ligand binding domain that can selectively bind to a surface LT ligand, and, more preferably, where the soluble LT-β-R comprises a human immunoglobulin FC domain.

In other embodiments, preferred blocking agents include monoclonal antibodies directed against the LT-β-R, including, preferably, anti-human LT-β-R mAb BDA8, and anit-human LT-β mAb B9. More preferred antibodies include A1.D5.18 and AO.D12.10. and BB-F6. In certain instances, it may be desirable to use a monclonal antibody directed against a murine surface LT ligand.

Figure 7:
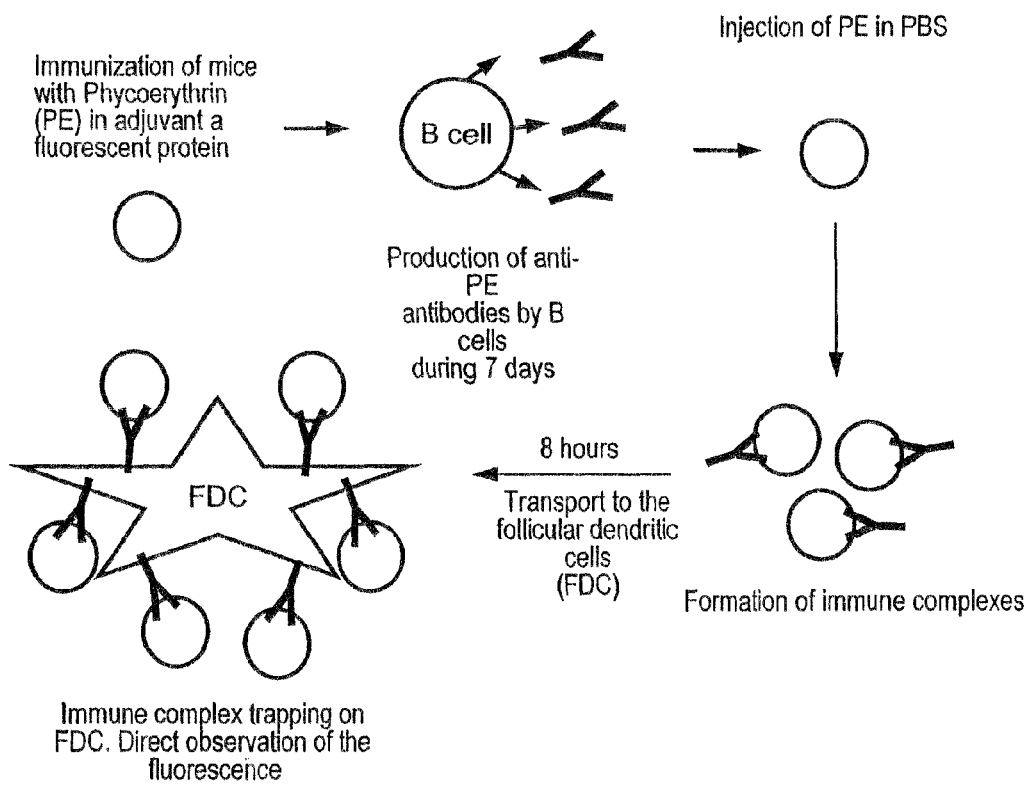
FIG. 7 is a representation of immune complex trapping on FDCs.

The long term presentation of antigen by FDCs is likely to be important in autoimmune diseases where the continual activation of the immune system by endogenous or autoantigens perpetuates the disease. Immune complex trapping on FDCs is illustrated in FIG. 7. The ability to remove these immune complexes from the FDC would serve to reduce the amount of immune activation and dampen the disease or even stop disease progression. Those autoimmune diseases that involve aberrant antibody responses are obvious targets for LT pathway inhibitors although other more "classically" T cell mediated autoimmune diseases may have unrecognized humoral components, and therefore may also be beneficially impacted.

Likewise, in the transplantation field, graft rejection, i.e., host vs. graft disease and graft vs. host disease, require the presentation of antigen to perpetuate. The mechanisms described here for manipulating FDC may also apply to those problems associated with the recognition of non-self, i.e. transplantation.

Additionally, the continued presentation of antigen or maintenance of antigen memory may play a role in those autoimmune diseases caused by molecular mimicry. For example, the immune reaction to the lyme disease infectious agent Borrelia burgdorferi leads to an arthritis-like disease presumably because some antigenic epitope on this bacterium resembles a normal joint component. Removal of the FDC-retained lyme bacterium antigen may ameliorate lyme disease induced arthritis. Such therapy would also be relevant to other cases of mimicry associated with infectious agents.

Applicants have surprisingly found that the administration of blocking agents of LT-β-R are capable of interfering with the presentation and/or deposition of antigens on follicular dendritic cells. Typically, B cells recognize antigen as immune complexes bound to the surface of follicular dendritic cells. Follicular dendritic cells may retain the antigens for an unspecified period of time. Periodical contact with the antigen retained on the FDC thus may be related to the memory retention of B cells. Thus, the claimed methods encompass numerous disease states which are dependent upon the presentation of antigen on dendritic cells. The administration of blocking agents of the invention can be done prior to introduction of antigen into an animal, in which case the blocking agents will prevent all or a portion of the deposition of the antigen on the follicular dendritic cells, thereby preventing, or diminishing, the expected immunogenic response. Alternatively, the blocking agents of the invention can be administered to an animal at a point after the follicular dendritic cells have antigen associated with them. Applicants claimed methods can disrupt this association, such that the expected immunogenic response would then be diminished or abolished. Thus, the therapeutic methods of the invention can involve the elimination in whole or in part of the immune complexes already trapped in B cell follicles, or, the prevention, in whole or in part, of the trapping of immune complexes on B cell follicles.

The ability to disrupt the association between these antigen presenting follicular dendritic cells and the immune complexes appears to be unique to the LT-β pathway. For example, anti-CD40L (MR-1) is another member of the TNF family and is also expressed on follicular dendritic cells. Like LT-β-R/Ig, MR-1 has been shown to prevent germinal cell formation, however, does not affect the expression of FDC markers. Anti-CD40-L, unlike LT-β-R, does not prevent immune complex trapping on follicular dendritic cells, nor is it able to eliminate immune complexes previously trapped on follicular dendritic cells. Additionally, applicants have shown that anti-CD40-L does not affect the survival/maintenance of previously generated memory B cells.

Although the precise basis for the differences beteween the impace of anti-CD-40L and LT-β-R blocking agents is not known, it is hypothesized that CD40 may provide survival signals to B cells. However, the LT system is critical to maintain follicular dendritic cells in a fully differentiated and functional state, a condition which appears to be necesary for germinal center reaction and memory B cell generation and maintenance. Thus, blocking the CD40/CD40L pathway may prevent generation of memory B cells, but will not affect the already established memory B cell pool. Blocking the LT pathway, on the other hand, prevents not only the generation and maintenance of memory B cells, but also affects the maintenance of previously generated memory B cells.

A further application of inhibition of the LT pathway lies in the treatment of viruses that form reservoirs in the follicular dendritic cell (FDC) compartment. The HIV virus is a good example of such a case. Following viral infection, large amounts of infectious virus reside on FDCs in the B cell follicles of the secondary lymphoid organs. (Heathe et al., 1995, "Follicular dendritic cells and human immunodeficiency virus infectivity.", Nature 377: 740-4). Virus is presumed to be complexed either with complement or immunoglobulin and bound to either Fc receptors or complement receptors or both. Thus, the virus exploits the normal mechanism of the immune system to retain antigen memory for long periods. During the course of the disease, active infection of lymphocytes occurs primarily at these sites. It has been calculated that during the asymptomatic phase of infection, the pool of virus in this compartment is more than 10 fold larger than that contained in T cells and monocytes. (Cavert et al., 1997, "Kinetics of response in lymphoid tissues to antiretroviral therapy of HIV-1 infection", Science 276:960-4). In current HIV treatment modalities, multiple anti-viral agents are combined to reduce the viral load and to avoid escape of resistant variants. A likely limitation of this therapy lies in non-compliance with the therapy and during such intervals, residual virus is free to mutate allowing the development of resistant variants and thus circumventing the therapy process. While the viral load in the FDC compartment is dramatically impacted during multiple drug therapy, the drugs themselves are largely directed at viral replication machinery, and not at the non-replicating virus on FDC surfaces. Therefore, the viral reservoir on FDCs can serve as a re-inoculum following cessation of drug therapy. Moreover, the FDCs can convert neutralized virus to an infectious form further underscoring the importance of these cells to HIV pathogenesis.

Since inhibition of the LT pathway can cause FDCs to release immune complexes from the cell surface, HIV in the form of an immune complex could also be released. It would be desirable to release all of the HIV load in this compartment immediately prior to commencement of multiple therapy type regimes as the released virus should either be processed and removed from the body or upon infection, it would be sensitive to the drug therapy. Such a combination could reduce the residual viral load to very low levels possibly effecting a cure. In this case, either LTβ-R/Ig or blocking antibodies to either the ligand or the receptor would be useful. A potential treatment protocol would involve initiating drug therapy, and then within several days, release any bound virus with one or several treatments with LT pathway inhibitors.

Once the viral load was reduced, further treatment with LT directed agents would not be required.

While HIV is a particularly well studied example, it is likely that other viruses reside or hide on FDCs in a quiescent state awaiting for some event such as an immunological disturbance which leads to large amounts of additional antigen load, and consequently the release of bound virus from FDCs and virus reemergence. Therefore, this invention relates to any means of Lt pathway inhibition to avoid the complications of FDC bound virus.

This discovery has significant implications for a number of diseases which rely on the presentation of antigen on dendritic cells, and response generated by memory B cells. LTα1/β2 signaling effectively and serves as an example of a therapeutically useful anti-LTb blocking monoclonal. Additionally, an anti-human LT alpha directed monoclonal antibody entitled A0D12 was able to block LTα1/β2 signaling well yet in contrast to most anti-human LT alpha monoclonal antibodies, it was poorly effective against LTα alone. These monoclonal antibodies were obtained following immunization of mice with soluble LTα1/β2 ligand leading to the discovery of monoclonal antibodies with unique specificity. Furthermore, we maintain that anti-LTα monoclonal antibodies with specificity directed preferentially against the LTα1/β2 complex will be found only following this form of immunization and not via immunization with LT alpha alone and hence comprises a unique class of anti-LTα antibodies.

EXAMPLES

Materials and Methods
Mice

Timed pregnant Balb/c mice were purchased from Jackson Laboratory (Bar Harbor, Me.), housed under conventional barrier protection, and handled in accordance with institutional guidelines. Receptor-Ig proteins or mAbs were injected into the tail vein (iv) of pregnant mice. Progeny of these mice and 5 week old female Balb/c mice (purchased from Jackson Laboratory, Bar Harbor, Me.) were injected with fusion proteins via the intraperitoneal (ip) route.

Fusion Proteins and Antibodies

Fusion proteins comprised of the extracellular domain of either murine LTβ-R, human TNF-R55 or human LFA-3 (which does not bind murine CD2) fused to the hinge, $C_H2$ and $C_H3$ domains of human IgG1 were prepared as described (Force et al., *J. Immunol.*, 155, pp. 5280-5288 (1995); Miller et al., *J. Exp. Med.*, 178, pp. 211-222 (1993)). Purified human IgG1 used as a control was purchased from Protos Immunoresearch (San Francisco, Calif.). MR1, anti-mouse CD40 ligand antibody, was purchased from Pharmingen (San Diego, Calif.).

Antibodies (MOMA-1, ED3) specific for markers expressed by mouse metallophilic macrophages (MM), (ED3 recognizes sialoadhesin), or specific for mouse reticular fibroblasts (ER-TR-7) were purchased from Serotec (Oxon, UK). Antibodies specific for mouse B220, CD4, and Mad-CAM-1 (MECA 367) were purchased from Pharmingen (San Diego, Calif.). An antibody (ER-TR-9) specific for a marker expressed by mouse marginal zone macrophages was provided by Dr. Reina Mebius (Vrije Universiteit, Amsterdam). Antibodies (FDC-M1 and FDC-M2) specific for mouse follicular dendritic cell (FDC) have been described previously (Maeda et al., *J. Immunol.*, 148, pp. 2340-2347 (1992)). Anti-mouse CR1 antibody (which also stains FDC) was kindly supplied by Dr. Randolph J. Noelle (Dartmouth Medical School). Detection of peripheral lymph node addressin (PNAd) utilized the antibody MECA 79 (cell culture supernatant derived from cells purchased from ATCC, Rockville, Md.).

Antigens and Immunizations

Mice were immunized ip with 100 μl of a 10% suspension of SRBC (purchased from the Colorado Serum Company). This is equivalent to $1-5 \times 10^8$ SRBC per immunization.

Immunohistochemistry

Spleen and lymph nodes were frozen in OCT embedding medium (Miles, Elkhart, Ind.) and mounted for cryostat sectioning. Sections 7-10 mm thick were dried and fixed with acetone. Sections were incubated with conjugated antibodies for 1 hr at room temperature in a humidified box after dilution in Tris buffered saline buffer A (TBS-A, 0.05M Tris, 0.15M NaCl, 0.05% Tween-20 (v/v), 0.25% bovine serum albumin (BSA)), rinsed in TBS-B (0.05M Tris, 0.15M NaCl, 0.05% Tween-20) and fixed 1 min in methanol before initiating the enzymatic reaction. Horseradish peroxidase (HRP) and alkaline phosphatase (AP) activities were developed using the DAB tablet substrate kit (Sigma, St. Louis, Mo.) and 5-bromo-4-chloro-3-indolyl phosphate/nitro blue tetrazolium (BCIP/NBT, Sigma), respectively. Tissue sections were fixed for 5 min in methanol and counter stained with Giemsa (Fluka, Buchs, Switzerland).

Fluorescence Image Analysis

For immunofluorescence staining, frozen sections were acetone fixed, air dried and preblocked with 5 μg/ml anti-CD16/CD32 Fc block (Pharmingen, San Diego Calif.) in Tris Buffered Saline with 0.25% BSA, 0.05% Tween-20 and 10% heat aggregated rabbit serum. Sections were stained in the same buffer using the following mAbs and detection reagents: 10 μg/ml biotinylated anti-B220 mAb (Pharmingen) followed by 20 μg/ml streptavidin-FITC (Southern Biotechnology Associates, Birmingham, Ala.); 10 μg/ml of MECA 367 followed by 10 μg/ml PE-goat F(ab')2 anti-rat IgG (Southern Biotechnology Associates); culture supernatant of MECA79 followed by 20 μg/ml FITC-mouse anti-rat IgM (Pharmingen); 20 μg/ml anti-Sialoahesin mAb followed by 10 μg/ml PE-goat F(ab')2 anti-rat IgG (Southern Biotechnology Associates), 50 μg/ml biotinylated PNA (Vector Laboratories, Burlingame, Calif.) followed by 10 μg/ml streptadvidin-PE (Southern Biotechnology Associates); 1:5 dilution of mAb MOMA-1 cell culture supernatant followed by 20 μg/ml FITC-mouse anti-rat IgM (Pharmingen). Some sections were stained with multiple mAbs simultaneously to allow image overlay analysis. All sections were viewed under 50× optics and photographed using Ektachrome P1600 (Kodak, Rochester, N.Y.) or captured as separate red and green image files as described (Rennert et al, *J. Exp. Med.* (November 1996, in press)).

Hemagglutination Assays

Serial dilutions of sera were made in 96 well microtiter plates (Costar, Cambridge, Mass.) in PBS/1% glucose. The SRBC-specific IgM titer was determined by adding 25 μl of a 10% SRBC suspension in each well and incubating the plate 1 hr in a humidified 37° C. incubator. For SRBC-specific IgG, sera was incubated for 30 min at 37° C. with 20 µl/well of 1% 2-mercaptoethanol (vol/vol) (Bio-Rad, Richmond, Calif.) to eliminate IgM pentamers. Then 25 µl/well of a 10% SRBC suspension was added, followed by 25 µl/well of a 10 mg/ml solution (in PBS/1% glucose) of goat anti-mouse IgG (Southern Biotechnology, Birmingham, Ala.) as a crosslinker agent for hemagglutination. The titer was determined as the reciprocal of last serum dilution for which hemagglutination is clearly apparent.

ELISAs

Analyses for receptor-Ig in plasma used mAbs specific for murine LTβ-R (Browning et al, manuscript in preparation), LFA-3 (Miller, et al., *J. Exp. Med.,* 178, pp. 211-222 (1993)) or the CH3 domain of human IgG$_1$ (CDG5, prepared at Biogen) directly immobilized (10 µg/ml) on 96 well microtiter plates for capture, and donkey anti-human IgG$_1$-Horse Radish Peroxidase (HRP) for detection (Jackson ImmunoResearch, West Grove Pa., 1:4000 dilution)

Production of Soluble LTβ-R Molecules

The LTβ-R blocking agents in one embodiment of this invention comprise soluble LTβ receptor molecules. FIG. 1 shows the sequence of the extracellular portion of the human LTβ-R, which encodes the ligand binding domain. Using the sequence information in FIG. 1 and recombinant DNA techniques well known in the art, functional fragments encoding the LTβ-R ligand binding domain can be cloned into a vector and expressed in an appropriate host to produce a soluble LTβ-R molecule. Soluble LTβ-R molecules that can compete with native LTβ receptors for LT ligand binding according to the assays described in applicants copending U.S. application Ser. No. 08/505,606, filed Jul. 21, 1995, are selected as LTβ-R blocking agents.

A soluble LTβ receptor comprising amino acid sequences selected from those shown in FIG. 1 may be attached to one or more heterologous protein domains ("fusion domain") to increase the in vivo stability of the receptor fusion protein, or to modulate its biological activity or localization.

Preferably, stable plasma proteins—which typically have a half-life greater than 20 hours in the circulation—are used to construct the receptor fusion proteins. Such plasma proteins include but are not limited to: immunoglobulins, serum albumin, lipoproteins, apolipoproteins and transferrin. Sequences that can target the soluble LTβ-R molecule to a particular cell or tissue type may also be attached to the LTβ-R ligand binding domain to create a specifically-localized soluble LTβ-R fusion protein.

All or a functional portion of the LTβ-R extracellular region (FIG. 1) comprising the LTβ-R ligand binding domain may be fused to an immunoglobulin constant region like the Fc domain of a human IgG1 heavy chain (Browning et al., *J. Immunol.,* 154, pp. 33-46 (1995)). Soluble receptor-IgG fusion proteins are preferable, and are common immunological reagents, and methods for their construction are known in the art (see e.g., U.S. Pat. No. 5,225,538 incorporated herein by reference).

A functional LTβ-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta, and to bind various microbial proteins. The properties of the different classes and subclasses of immunoglobulins are described in Roitt et al., *Immunology,* p. 4.8 (Mosby-Year Book Europe Ltd., 3d ed. 1993).

Activation of the complement system initiates cascades of enzymatic reactions that mediate inflammation. The products of the complement system have a variety of functions, including binding of bacteria, endocytosis, phagocytosis, cytotoxicity, free radical production and solubilization of immune complexes.

The complement enzyme cascade can be activated by the Fc domains of antigen-bound IgG1, IgG3 and IgM antibodies. The Fc domain of IgG2 appears to be less effective, and the Fc domains of IgG4, IgA, IgD and IgE are ineffective at activating complement. Thus one can select a Fc domain based on whether its associated secondary effector functions are desirable for the particular immune response or disease being treated with the LTβ-R-Ig fusion protein.

If it would be advantageous to harm or kill the LT ligand-bearing target cell, one could select an especially active Fc domain (IgG1) to make the LTβR-Ig fusion protein. Alternatively, if it would be desirable to target the LTβR-Fc fusion to a cell without triggering the complement system, an inactive IgG4 Fc domain could be selected.

Mutations in Fc domains that reduce or eliminate binding to Fc receptors and complement activation have been described (S. Morrison, *Annu. Rev. Immunol.,* 10, pp. 239-65 (1992)). These or other mutations can be used, alone or in combination, to optimize the activity of the Fc domain used to construct the LTβ-R-Ig fusion protein.

The production of a soluble human LTβ-R fusion protein comprising ligand binding sequences fused to a human immunoglobulin Fc domain (hLTβ-R-Ig) is described in Example 1. One CHO line made according to Example 1 that secretes hLTβ-R-Fc is called "hLTβ-R; hG1 CHO#14". A sample of this line was deposited on Jul. 21, 1995 with the American Type Culture Collection (ATCC) (Rockville, Md.) according to the provisions of the Budapest Treaty and was assigned the ATCC accession number CRL11965.

The production of a soluble murine LTβ-R fusion molecule (LTβ-R-Ig) is described in Example 2. A CHO line made according to Example 2 that secretes LTβ-R-Ig is called "mLTβ; R-hG1CHO#1.3.BB". A sample of this line was deposited on Jul. 21, 1995 with the American Type Culture Collection (ATCC) (Rockville, Md.) according to the provisions of the Budapest Treaty and was assigned the ATCC accession number CRL11964.

All restrictions on the availability to the public of the above ATCC deposits will be irrevocably removed upon the granting of a patent on this application.

Different amino acid residues forming the junction point of the receptor-Ig fusion protein may alter the structure, stability and ultimate biological activity of the soluble LTβ receptor fusion protein. One or more amino acids may be added to the C-terminus of the selected LTβ-R fragment to modify the junction point with the selected fusion domain.

The N-terminus of the LTβ-R fusion protein may also be varied by changing the position at which the selected LTβ-R DNA fragment is cleaved at its 5' end for insertion into the recombinant expression vector. The stability and activity of each LTβ-R fusion protein may be tested and optimized using routine experimentation and the assays for selecting LTβ-R blocking agents described herein.

Using the LTβ-R ligand binding domain sequences within the extracellular domain shown in FIG. 1, amino acid sequence variants may also be constructed to modify the affinity of the soluble LTβ receptor or fusion protein for LT ligand. The soluble LTβ-R molecules of this invention can compete for surface LT ligand binding with endogenous cell surface LTβ receptors. It is envisioned that any soluble molecule comprising a LTβ-R ligand binding domain that can compete with cell surface LTβ receptors for LT ligand binding is a LTβ-R blocking agent that falls within the scope of the present invention.

Source of Anti-LTβ-R Antibodies

In another embodiment of this invention, antibodies directed against the human LTβ receptor (anti-LTβ-R Abs) function as LTβ-R blocking agents. The anti-LTβ-R Abs of this invention can be polyclonal or monoclonal (mAbs) and can be modified to optimize their ability to block LTβ-R signalling, their in vivo bioavailability, stability, or other desired traits.

Polyclonal antibody sera directed against the human LTβ receptor are prepared using conventional techniques by injecting animals such as goats, rabbits, rats, hamsters or mice subcutaneously with a human LTβ receptor-Ig fusion protein (Example 1) in complete Freund's adjuvant, followed by booster intraperitoneal or subcutaneous injection in incomplete Freund's.

Polyclonal antisera containing the desired antibodies directed against the LTβ receptor are screened by conventional immunological procedures.

Mouse monoclonal antibodies (mAbs) directed against a human LTβ receptor-Ig fusion protein are prepared as described in applicants copending U.S. application Ser. No. 08/505,606, filed Jul. 21, 1995. A hybridoma cell line (BD.A8.AB9) which produces the mouse anti-human LTβ-R mAb BDA8 was deposited on Jan. 12, 1995 with the American Type Culture Collection (ATCC) (Rockville, Md.) according to the provisions of the Budapest Treaty, and was assigned the ATCC accession number HB11798. All restrictions on the availability to the public of the above ATCC deposits will be irrevocably removed upon the granting of a patent on this application.

Various forms of anti-LTβ-R antibodies can also be made using standard recombinant DNA techniques (Winter and Milstein, Nature, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., Proc. Natl. Acad. Sci. U.S.A., 81, pp. 6851-55 (1984)). Chimeric antibodies reduce the observed immunogenic responses elicited by animal antibodies when used in human clinical treatments.

In addition, recombinant "humanized antibodies" which recognize the LTβ-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LTβ-R antibodies can also be accomplished by making chimeric or humanized antibodies comprising the anti-LTβ-R variable domains and human constant domains (CH1, CH2, CH3) isolated from different classes of immunoglobulins. For example, anti-LTβ-R IgM antibodies with increased antigen binding site valencies can be recombinantly produced by cloning the antigen binding site into vectors carrying the human μ chain constant regions (Arulanandam et al., J. Exp. Med., 177, pp. 1439-50 (1993); Lane et al., Eur. J. Immunol., 22, pp. 2573-78 (1993); Traunecker et al., Nature, 339, pp. 68-70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling (Queen et al., Proc. Natl. Acad. Sci. U.S.A., 86, pp. 10029-33 (1989); WO 94/04679).

It may be desirable to increase or to decrease the affinity of anti-LTβ-R Abs for the LTβ-R depending on the targeted tissue type or the particular treatment schedule envisioned. For example, it may be advantageous to treat a patient with constant levels of anti-LTβ-R Abs with reduced ability to signal through the LT-β pathway for semi-prophylactic treatments. Likewise, inhibitory anti-LTβ-R Abs with increased affinity for the LTβ-R may be advantageous for short-term treatments.

Source of Anti-Surface LT Ligand Antibodies

Another preferred embodiment of this invention involves compositions and methods which comprise antibodies directed against LT ligand that function as LTβ-R blocking agents. As described above for the anti-LTβ-R Abs, anti-LT ligand antibodies that function as LTβ-R blocking agents can be polyclonal or monoclonal, and can be modified according to routine procedures to modulate their antigen binding properties and their immunogenicity.

The anti-LT antibodies of this invention can be raised against either one of the two LT subunits individually, including soluble, mutant, altered and chimeric forms of the LT subunit. If LT subunits are used as the antigen, preferably they are LTβ subunits. If LTα subunits are used, it is preferred that the resulting anti-LTα antibodies bind to surface LT ligand and do not cross-react with secreted LTα or modulate TNF-R activity (according to the assays described in applicants copending U.S. application Ser. No. 08/505,606, filed Jul. 21, 1995).

Alternatively, antibodies directed against a homomeric (LTβ or a heteromeric (LTα/β) complex comprising one or more LT subunits can be raised and screened for activity as LTβ-R blocking agents. Preferably, LTα1/β2 complexes are used as the antigen. As discussed above, it is preferred that the resulting anti-LTα1/β2 antibodies bind to surface LT ligand without binding to secreted LTα and without affecting TNF-R activity.

The production of polyclonal anti-human LTα antibodies is described in applicants' co-pending application (WO 94/13808). Monoclonal anti-LTa and anti-LTβ antibodies have also been described (Browning et al., J. Immunol., 154, pp. 33-46 (1995)).

Mouse anti-human LTβ mAbs were prepared as described in applicants copending U.S. application Ser. No. 08/505,606, filed Jul. 21, 1995. A hybridoma cell line (B9.C9.1) which produces the mouse anti-human LTβ-R mAb B9 was deposited on Jul. 21, 1995 with the American Type Culture Collection (ATCC) (Rockville, Md.) according to the provisions of the Budapest Treaty, and was assigned the ATCC accession number HB11962.

Monoclonal hamster anti-mouse LTα/β antibodies were prepared as described in applicants copending U.S. application Ser. No. 08/505,606, filed Jul. 21, 1995. A hybridoma cell line (BB.F6.1) which produces the hamster anti-mouse LTα/β mAb BB.F6 was deposited on Jul. 21, 1995 with the American Type Culture Collection (ATCC) (Rockville, Md.) according to the provisions of the Budapest Treaty, and was assigned the ATCC accession number HB11963.

All restrictions on the availability to the public of the above ATCC deposits will be irrevocably removed upon the granting of a patent on this application.

Use of soluble LTβ-R-Ig to inhibit the immunological functions of the surface LT complex. We now show effects of a surface LT binding reagent, a fusion protein comprised of the extracellular domain of murine LTβ-R and the hinge, CH2 and CH3 domains of human IgG1 (LTβ-R-Ig), on the generation and character of immunoglobulin responses, on the maintenance of the cellular organization of secondary lymphoid tissues including effects on the differentiation state of follicular dendritic cells and germinal center formation, and on addressin expression levels which influence cell trafficking.

Multiple injections of mice with LTβ-R-Ig alters the organization of splenic lymphocytes and the expression of functional markers by splenic marginal zone cells.

The effect of surface LT blockade on the structure of the spleen was examined by giving mice six consecutive weekly injections of LTβ-R-Ig. Mice were then immunized with SRBC and given an additional injection of LTβ-R-Ig 4 days later. Mice were sacrificed on day 10 after SRBC injection. Immunohistochemical staining of frozen spleen sections revealed several histologic changes. The follicles which comprise the splenic B cell compartment in normal mice are no longer discrete following LTβ-R-Ig treatment. Instead B cells are now organized in a diffuse band surrounding the T cell areas (FIG. 2B), and the boundary between the T and B cell zones is disrupted (FIG. 2B). In contrast, in the control LFA-3-Ig treated mice the splenic B-cell follicles are discrete and there is a clear demarcation between T and B cell areas (FIG. 2A). Expression of cell surface markers recognized by the monoclonal antibodies ER-TR-9 and MOMA-1 is absent from two distinct macrophage populations residing in the splenic marginal zone of LTβ-R-Ig treated mice. ER-TR-9 is known to stain a marker on MZM (Dijkstra et al., *Immunol.*, 55, 23-30 (1985)) and MOMA-1 stains a marker on metallophilic macrophages (Kraal and Janse, Immunol., 58, 665-669, (1986)) (FIG. 2 D, F, respectively). These markers are expressed on cells in control (LFA-3-Ig) treated mice (FIG. 2 C, E). Expression of sialoadhesin, another marker of M0MA-1+ macrophages in the murine splenic marginal zone, is also absent in LTβ-R-Ig treated mice (data not shown).

The antibody MECA-367 binds the adhesion molecule and mucosal addressin MAdCAM-1, originally described on endothelial cells in Peyer's patches, mesenteric lymph nodes, the intestinal mucosa and lamina propria (Briskin et al., *Nature*, 363, pp. 461-464 (1993); Nakache et al., *Nature*, 337, pp. 179-181 (1989)). MAdCAM-1 expression has also been described in the splenic marginal zone (presumably expressed on the endothelial cells of the small terminal arterioles opening onto the marginal sinus) and on the reticular meshwork within the germinal centers (Kraal et al., *Am. J. Pathol.*, 147, pp. 763-771 (1995)) (FIG. 2G). MECA 367 staining of sections from LTβ-R-Ig treated mice show that MAdCAM-1 expression has been extinguished in the spleen (FIG. 2H).

Likewise, the staining by the ER-TR-7 antibody (Van Vliet et al., *Cytochem.*, 34, pp. 883-890 (1986)) which delineates a population of reticular fibroblasts in the marginal zone (FIG. 2I), is abnormally distributed and stronger in the white pulp of the LTβ-R-Ig than LFA-3-Ig treated animals (FIG. 2J). The changes observed in LTβ-R-Ig treated mice were independent of antigen exposure as the pattern of staining was identical in LTβ-R-Ig treated unimmunized mice (data not shown).

Germinal Center Formation is Ablated and Follicular Dendritic Cells are not Detected in the Spleens of LTβ-R-Ig Treated Mice.

Figure 3C:
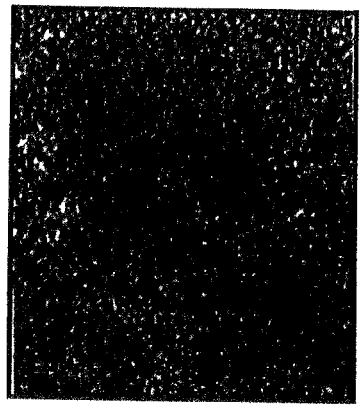
FIG. 3 is an immunohistochemical analysis showing the absence of germinal centers from spleens of LTβ-R-Ig treated and MR-1 (anti-CD40 ligand antibody) treated mice, and the presence of follicular dendritic cells in spleens of MR-1 but not LTβ-R-Ig treated mice. Fusion proteins and SRBC antigen were administered as described for FIG. 2.
Figure 3F:
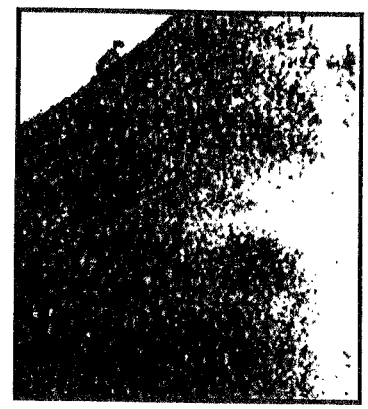
Figure 3B:
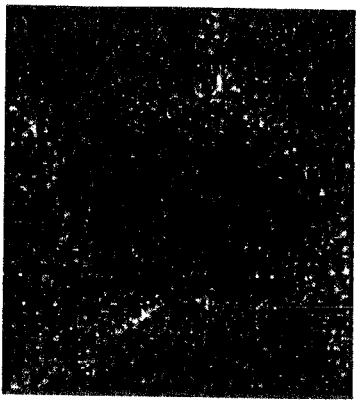
Figure 3E:
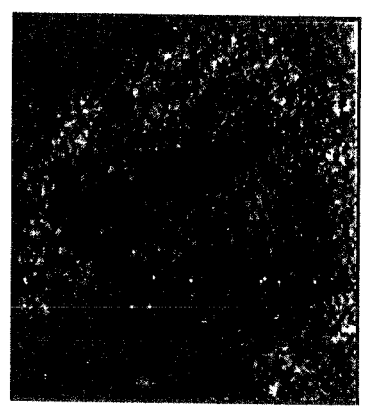
Figure 3A:
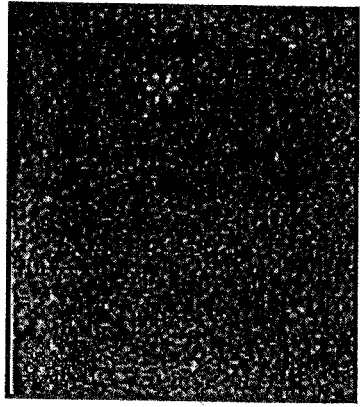
Figure 3D:
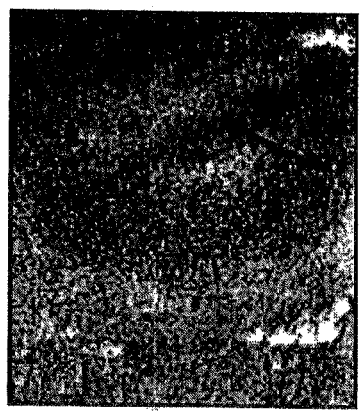
Figure 4A:
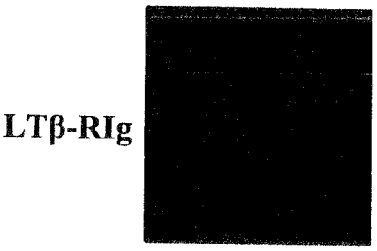
FIG. 4 is an immunohistochemical analysis showing addressin expression is altered in LN of mice treated in utero and continuously post-birth with LTβ-R-Ig.
Figure 4B:
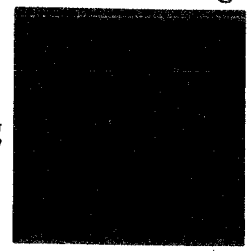
Figure 4C:
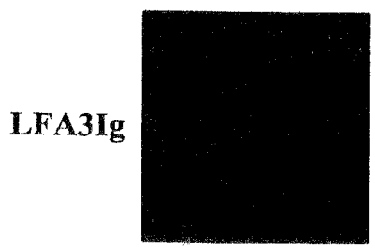
Figure 4D:
Figure 4E:
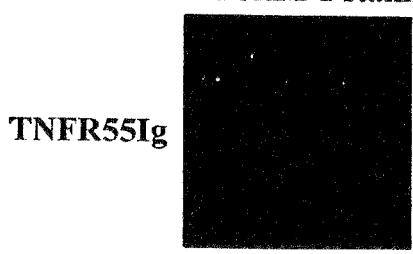
Figure 4F:
Figure 4G:
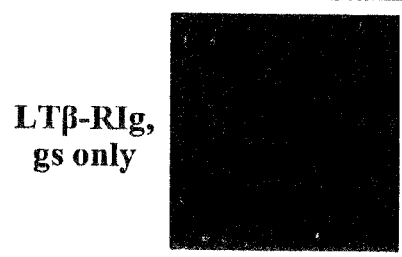
Figure 4H:
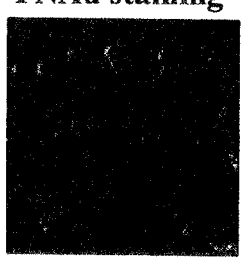

To determine at the histologic level whether multiple injections of mice of LTβ-R-Ig affects the immune response to SRBC, an analysis of germinal center (GC) formation and follicular dendritic cell (FDC) distribution in response to antigen priming was performed. Frozen spleen sections from mice pretreated multiple times with LTβ-R-Ig or LFA-3-Ig as described for FIG. 2, were stained with peanut agglutinin (PNA) to delineate the GCs and with the FDC-M1 antibody to detect FDC, a cellular component required for GC formation (Schriever and Nadler, *Adv. Immunol.*, 51, pp. 243-284 (1992); Tew et al., *Immunol. Rev.*, 117, pp. 185-211 (1990)). The CD40-CD40 ligand interaction has also been shown to be critical for GC formation (Foy et al., *J. Exp. Med.*, 180, pp. 157-163 (1994)). Thus for comparison, a group of mice was treated with MR1, an anti-mouse CD40 ligand antibody, following an injection protocol which has previously been shown to inhibit GC formation (Han et al., *J. Immunol.*, 155, pp. 556-567 (1995)). Ten days after SRBC challenge, mice treated with the control LFA-3-Ig protein developed numerous PNA bright GC in the spleen (FIG. 3A). GC were not detected in the spleen of LTβ-R-Ig or MR1-treated mice (FIG. 3 B,C respectively). However, the effect of MR1 and LTβ-R-Ig can be distinguished by two additional observations. The staining for FDCs (FDC-M1) within the GC (FIG. 3D) is absent in the spleen of LTβ-R-Ig treated mice (FIG. 3E) but still present in the spleen of MR1-treated mice (FIG. 3F). Similar observations was made using the FDC-M2 antibody to stain FDCs (data not shown). Thus LTβ-R-Ig treatment results in the phenotypic alteration of FDC in the spleen and the failure to form GC.

In addition to staining GC, PNA also stains the marginal zone in the spleen of normal mice. Such staining was also noted in LFA-3-Ig treated (FIG. 3A) and MR1-treated mice (FIG. 3C), but was absent in the spleen of LTβ-R-Ig treated mice (FIG. 3B).

The expression of sialoadhesin, MOMA-1, ER-TR-9, ER-TR-7 and MAdCAM-1 in the spleen of MR1-treated mice was also shown to be normal (data not shown), further distinguishing the molecular effects of interfering with CD40 and LTβ-R signaling.

Kinetics of LTβ-R-Ig Induced Alterations of Splenic Lymphocyte Organization and Marginal Zone Cell Markers Expression The number of LTβ-R-Ig injections required to affect lymphocyte organization and expression of marginal zone cell markers in the spleen was analyzed. Mice were injected ip with LTβ-R-Ig either once or multiple times as indicated in Table 1. Some mice were then also immunized with SRBC on the day of the last LTβ-R-Ig injection. B220 and CD4 expression on B and T cells, respectively, and staining with PNA (for GC) and MECA367 (for MAdCAM-1), MOMA-1, ER-TR-9, and FDC-M1 was assessed on frozen spleen sections from treated mice. The kinetics of disappearance for the staining of metallophilic macrophages, marginal zone macrophages, MAdCAM-1, GCs and FDCs are shown to be distinct.

One injection of LTβ-R-Ig is sufficient to eliminate MAdCAM-1 staining a week later. Following three weekly LTβ-R-Ig injections, staining for GCs and FDCs is not detected and the T/B lymphocyte compartments are disrupted. A minimum of four LTβ-R-Ig injections are required to abolish the staining for metallophilic macrophages. Six LTβ-R-Ig injections do not completely ablate staining of marginal zone macrophages with ER-TR-9 antibody (also illustrated in FIG. 2 D).

A more precise analysis of the rapid inhibition of MOMA-1, MAdCAM-1, FDC-M1, FDC-M2 and CR1 staining following a single injection of LTβ-R-Ig was done in the absence of antigen (Table 2).

TABLE 1

Effect of LTβ-R-Ig on splenic organization of germinal center formation in response to SRBC in adult mice

| Number of LTβ-R-Ig injections | T/B cell organization | Metallophilic macrophages* | Marginal zone macrophages* | MAdCAM-1 Expression* | Germinal Centers§ | FDC* |
|---|---|---|---|---|---|---|
| 0 | normal | +++ | +++ | +++ | +++ | +++ |
| 1 | normal | ++ | +++ | − | + | + |
| 2 | slightly abnormal | + | +++ | − | + | +/− |
| 3‡ | disrupted | + | ++ | − | ND | ND |
| 4‡ | disrupted | +/− | ++ | − | ND | ND |
| 5‡ | disrupted | − | + | − | ND | ND |
| 6 | disrupted | − | +/− | − | − | − |

Mice were injected ip with 100 μg of LTβ-R-Ig every week for 1 to 5 weeks and then sacrificed. LTβ-R-Ig was administered prior to SRBC ip injection (100 μl of a 10% suspension) unless otherwise indicated, and the last LTβ-R-Ig injection was given the same day as antigen. Animals were sacrificed 10 days after SRBC injection. Frozen spleen sections were double stained with biotinylated rat anti-mouse B220 and rat anti-mouse CD4, followed by streptavidin-alkaline phosphatase and mouse anti-rat Ig-peroxidase respectively. Spleen sections were also stained with the following anti-mouse antibodies: rat anti-marginal zone macrophages (ER-TR9), rat anti-metallophilic macrophages (MOMA-1), rat anti-MAdCAM-1 (MECA 367) and rat anti-FDC (FDC-M1), followed by a mouse anti-rat Ig-peroxidase. An additional set of frozen sections was stained with biotinylated peanut agglutinine (PNA-biotin), followed by staining with streptavidin-peroxidase to detect germinal centers. Observations were made on sections from at least 3 animals per group.
*The intensity of the staining was estimated by eye: normal staining: +++, reduced staining ++, weak staining +, and no staining −. The intensity of the staining on sections from non-treated animals and animals treated with LFA-3-Lg was taken as a reference for the normal staining.
§The number of germinal centers per spleen section is recorded as follows: >10: +++; 5-10: ++; 1-5: +; none: −.
‡Animals from these groups did not receive SRBC.
ND: not done

TABLE 2

Precise timing of LTβ-R-Ig effects on the MOMA-1, MAdCAM-1, CR1, FDC-M1 and FDC-M2 staining

| | DAYS AFTER A SINGLE INJECTION OF LTβ-R-Ig | | | | | | |
|---|---|---|---|---|---|---|---|
| | 0 | 1 | 3 | 5 | 7 | 10 | 14 |
| MOMA-1* | +++ | +++ | +++ | +++ | ++ | ++ | + |
| MAdCAM-1* | +++ | +/− | − | − | − | − | − |
| CR1* | +++ | +++ | ++ | ++ | ++ | ++ | + |
| FDC-M1* | +++ | +/− | − | − | − | − | − |
| FDC-M2* | +++ | +/− | − | − | − | − | − |

*The intensity of the staining was estimated by eye: normal staining: +++, reduced staining ++, weak staining +, and no staining −. The staining intensity on sections from untreated animals and animals treated with human Ig was taken as a reference for the normal staining. Sections from at least 2 animals per group were analyzed.

Balb/c mice, 5-6 weeks received one ip injection of 100 μg of LTβ-R-Ig or human Ig. Mice from each group were sacrificed on day 0, 1, 3, 5, 7, 10 and 14. Frozen spleen sections were stained with the following antibodies: rat anti-mouse metallophilic macrophages (MOMA-1), rat anti-mouse MAdCAM-1 (MECA 367), rat anti-mouse FDC (FDC-M1), rat anti-mouse FDC (FDC-M2) and biotin-labeled rat anti-mouse CR1 followed by a mouse anti-rat Ig-peroxidase (MOMA-1, MAdCAM-1, FDC-M1 and FDC-M2) or peroxidase-labeled streptavidin (CR1).

Balb/c mice which received a single ip injection of LTβ-R-Ig were sacrificed every day for fourteen days after injection and their spleens were removed and frozen. Frozen spleen sections were stained with MOMA-1, anti-MAdCAM-1 (MECA-367), and FDC specific reagents: FDC-M1, FDC-M2 and anti-CR1 antibodies. One day after LTβ-R-Ig injection, staining with anti-MAdCAM-1 FDC-M1 and FDC-M2 reagents was greatly reduced (Table 2). The faster inhibition of FDC-M1 staining in this experiment compared to results described in Table 1 may be due to the intensity of FDC-M1 staining which is stronger in immunized animals. Staining for CR1 was still detectable at day 14 indicating that the FDC were still present on day 3 after treatment with LTβ-R-Ig but that the expression of markers detected with FDC-M1 and FDC-M2 was extinguished. Thus LTβR-Ig treatment altered the FDC phenotype. Finally, MOMA-1 staining was reduced but still detected at day 14.

Multiple LTβ-R-Ig Treatments Inhibit Addressin Expression in LN.

We examined addressin expression in LN of the progeny of timed pregnant Balb/c mice which were injected iv on days 14 and 17 of gestation with 200 μg of receptor-Ig proteins. After birth the progeny were either untreated or injected once per week with 100 μg of LTβ-R-Ig, TNF-R55—Ig, or LFA-3-Ig ip. Fusion protein levels remained at or above 10 μg/ml throughout life as determined by ELISA (data not shown). Immunohistochemical staining with MECA367 and MECA79 showed that MAdCAM-1 and peripheral LN addressins were entirely absent in mesenteric LN from mice treated throughout life with LTβ-R-Ig (FIG. 4 A, B). Sacral LN from these mice also lacked expression of all addressins and the cervical and iliac LN did not show peripheral lymph node (PNAd) staining (data not shown). The downregulation of addressin expression was reversible, since expression recovered to normal levels in animals which were treated only in utero (FIG. 4 G, H). In mice treated throughout life with 100 μg/week TNF-R55-Ig or LFA-3-Ig, addressin expression in LN remained comparable to untreated mice (FIG. 4 C,D, E,F).

B Lymphocyte Positioning and Macrophage Marker Expression is Altered in LN of LTβ-R-Ig Treated Mice.

Antibodies which bind markers on macrophage populations in the LN subcapsular sinus (analogous to the splenic marginal zone) were used to do immunohistochemical analysis of LN taken from mice which had been treated during gestation and continuously after birth as described for FIG. 4 above with LTβ-R-Ig, TNF-R55—Ig, or LFA-3-Ig. Fluorescent images were analyzed using image analysis software. Sialoadhesin expression is shown to be diminished in LN of mice treated with soluble LTβ-R-Ig (FIG. 5 B), but not in LN of TNF-R55—Ig or LFA-3-Ig mice (FIG. 5 E, H). MOMA-1 expression on macrophages in the subcapsular sinus was still detected in LN of mice treated with LTβ-R-Ig (FIG. 5 C).

Effects of continuous LTβ-R-Ig treatment on lymphocyte organization in LN were also evaluated. LN sections were stained with mAbs specific for the B cell marker B220 and the T cell marker CD4. Image analysis was used in order to identify areas of overlap of T and B cell zones. Treatment with LTβ-R-Ig caused the dissolution of B cell follicles such that the B cells were present in a diffuse band on the outer margin of the T cell area (FIG. 5 A). Despite the dissolution of their follicular structure, B cells were not present within T cell areas of the LN, instead they appeared in areas not normally occupied by lymphocytes. A very similar pattern of T and B cell staining was observed in mice treated throughout life with 100 μg/week TNF-R55-Ig, but not LFA-3-Ig (FIG. 5 D). Again B cell follicles were disrupted and B cells were present in areas of the LN not usually found to contain lymphocytes. Overlap of B cells with T cells was not observed.

LTβ-R-Ig Treatment of Mice Inhibits the IgM and IgG Antibody Response.

Figure 6A:
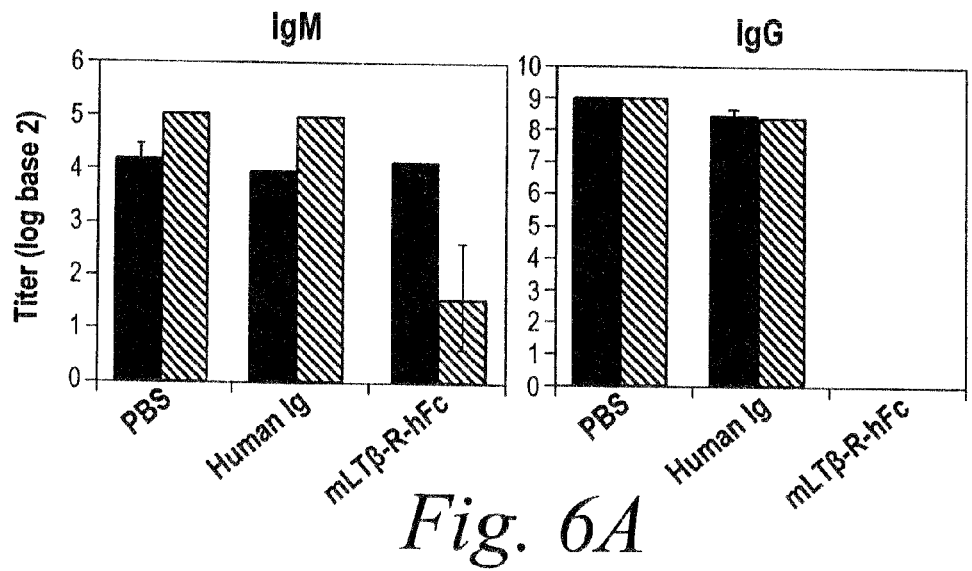
FIG. 6 is an immunohistochemical analysis showing that LTβ-R-Ig treatment of mice inhibits the antibody response to SRBC.

The failure of splenic GC to form following SRBC priming of mice treated multiple times with LTβ-R-Ig (as in FIG. 3) suggested alterations in the humoral immune response of these mice. To test this directly adult mice received six injections, once weekly, of LTβ-R-Ig or LFA-3-Ig and were then primed with SRBC. Mice were bled on days 7 and 14 postimmunization and the presence of SRBC-specific IgM and IgG in the sera was analyzed using hemagglutination assays. Seven days after SRBC immunization the IgM titer is normal but the IgG response is greatly diminished in LTβ-R-Ig treated mice as compared to mice treated with human Ig or PBS. (FIG. 6A). On day 14 postimmunization, SRBC specific IgG still is not detected in the sera from LTβ-R-Ig treated mice and the titer of SRBC specific IgM in these mice is also decreased by more than half compared to human Ig or PBS treated mice (FIG. 6A).

Figure 6B:
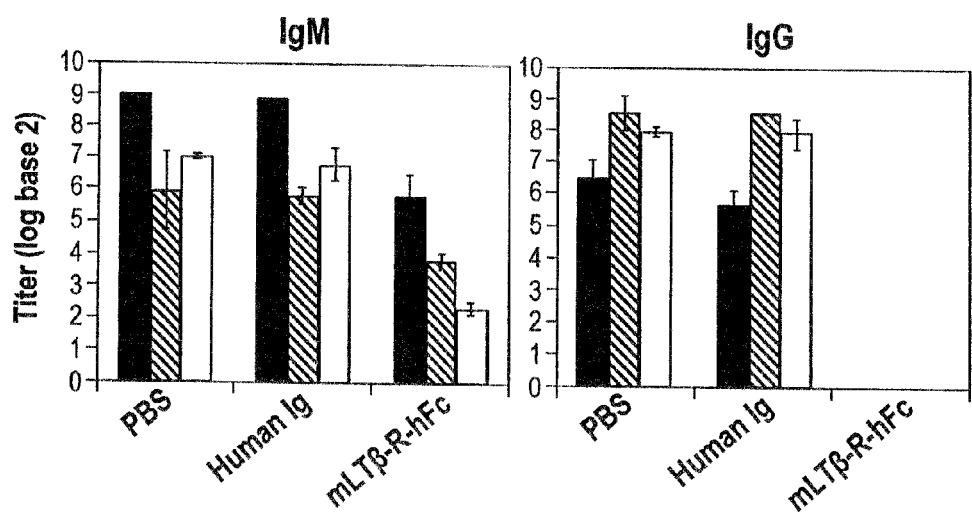

Ten days after SRBC priming GCs are detected in the spleens of mice treated once or twice with LTβ-R-Ig, however the number of GCs is greatly diminished compared to controls (Table 1). When mice received two injections of LTβ-R-Ig, the first injection a week before SRBC priming, and the second injection the same day as SRBC injection, the inhibition of the IgM and IgG response to SRBC at day 7 and day 14 (FIG. 6B) is similar to that detected when mice received multiple LTβ-R-Ig injections (FIG. 6A). At day 30 postimmunization, SRBC-specific IgG is not detected and the IgM levels are reduced by more than 80% compared to controls (FIG. 6 B). Thus these LTβ-R-Ig treatment protocols resulted in the complete inhibition of IgG responses, and an abbreviated/diminished IgM response relative to the controls.

Figure 6C:
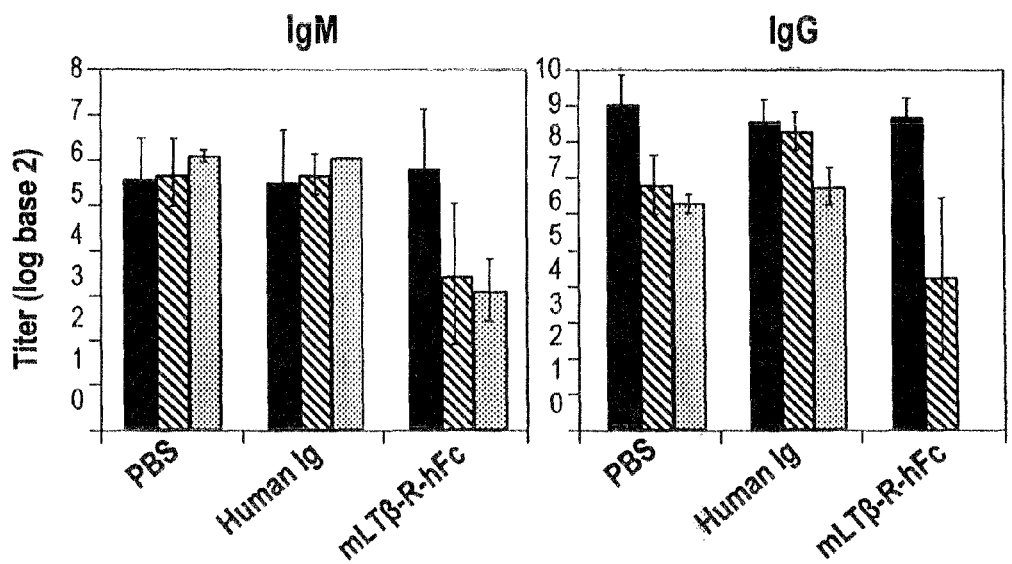

When mice received a single injection of LTβ-R-Ig on the same day as SRBC priming, the level of the IgG and IgM responses to SRBC on day 7 was comparable to that of the control groups (FIG. 6C). However, on day 24 postimmunization the IgM and IgG titers are both reduced by 30%. At day 34 after SRBC priming, the titer of SRBC-specific IgM is reduced by 50% compared to control groups and SRBC-specific IgG could not be detected (FIG. 6C). These data show that this LTβ-R-Ig treatment protocol resulted in the marked abbreviation/reduction of the levels of both an ongoing IgM and IgG response, that is that LTβ-R-Ig treatment can inhibit a humoral response which has already been initiated.

Antibody Mediated Diseases

Many organ-specific and multisystem autoimmune conditions involve pathological antibody responses. Such conditions include: Myasthenia Gravis, autoimmune hemolytic anemia, Chagas' disease, Grave's disease, idiopathic thrombocytopenia purpura (ITP) Systemic Lupus Erythematosus (SLE), Wegener's Granulomatosis, Poly-arteritis Nodosa and Rapidly Progressive Crescentic Glomerulonephritis. (From Benjamini, et al. *Immunology, A Short Course*. (Wiley-Liss, New York 3d ed. (1996))

Although the etiology of SLE is undefined, a fair amount is known about the immunologic mechanism responsible for the pathology observed. For unknown reasons, patients with SLE produce antibodies against nuclear components of the body (antinuclear antibodies (ANA) notably against native double stranded DNA. Clinically the presence of these antibodies correlates best with the pathology of renal involvement in SLE. These antibodies complex with DNA apparently derived from the breakdown of normal tissue, and as in any immune-aggregate disease, such complexes form deposits trapped against the basement membrane of the glomeruli, in arteriolar walls and in joint synovial spaces. These complexes activate the complement cascade and attract granulocytes. The subsequent inflammatory reaction is characterized as glomerulonephritis, with resulting damage to the kidneys leading to proteinuria and hematuria.

Lupus nephritis has been studied in murine models for decades. Recently, the therapeutic efficacy of a reagent specific for the murine CD40 ligand was evaluated in such a model (Mohan, et al., *J. Immunol.*, 154, pp. 1470-1480 (1995)). The acceleration of lupus by the transfer of cells which induce the production of pathogenic antibodies in vivo was shown to be inhibited by administration of a monoclonal antibody which blocks CD40/CD40 ligand interactions. Moreover a brief treatment of lupus mice with anti-CD40 ligand antibody had a sustained beneficial effect on their spontaneous disease long after the antibody had been cleared from their systems. The experimentation indicated that pathogenic B cells could not produce antibody even 9 months after the therapy suggesting that there was a delay of the expansion of autoimmune memory B cells resulting in long-term therapeutic benefits. As we have shown that reagents which block LTα/β/LT13-R interactions in vivo inhibit the generation of antibody responses, alter the phenotype of FDC and the formation of germinal centers involved in optimal generation of B cell memory, the LTα/β/LTβ-R blocking reagents of this invention will be useful for treating or preventing SLE.

The normal immune response to some pathogenic infectious agents also elicits autoantibody responses that can become excessive and present a medical problem. One example is Chagas' disease, an inflammatory cardiomyopathy which develops in humans and experimental animals with chronic *Trypanosoma cruzi* infection. Among the possible mechanisms involved in the pathogenesis of human Chagas' cardio-myopathy, induction of heart—specific autoimmune responses has recently received substantial experimental support. A recent study (Tibbetts, et al., *J. Immunol.*, 152, pp. 1493-1499 (1994)) determined that cardiac antigen-specific antibodies are produced in *T. Cruzi*-infected C57B1/6 mice with heart disease. Upon infection with the Brazil strain of *T. Cruzi*, C57B1/6 mice develop a cardiomyopathy that is histologically similar to that observed in chronically infected humans. Antisera from these mice react with three cardiac antigens while C57B1/6 mice infected with the Guayas strain of *T Cruzi* which do not develop cardiomyopathy did not produce such antibodies. These data indicate that these antibodies are specific markers of cardiomyopathy. Thus the ability of LTβ-R blocking agents to inhibit damage mediated by autoantibodies can be assessed in such a rodent model.

Another example of cell destruction by autoantibodies generated as a consequence of certain infectious diseases or for other unknown reasons is idiopathic thrombocytopenia purpura (ITP). In this condition antibodies directed to platelets result in platelet destruction (by complement or phagocytic cells with Fc or C3b receptor) which may lead to bleeding.

Therapeutics which will inhibit such antibody mediated autoimmune reactions in vivo such as the LT-β-R blocking agents of this invention—which inhibit antibody generation—will be useful to treat or prevent these autoimmune diseases as well.

The normal immune response to some pathogenic infectious agents also elicits hypersensitivity reactions that can become excessive and present itself as a medical problem. The most prevalent example of type I hypersensitivity is allergic reaction. These are mediated by IgE antibodies which bind via their Fc portion to receptors on mast cells and basophils to trigger the release of pharmacologically active agents that mediate anaphylaxis. ITP and Goodpasture's syndrome are sometimes thought to be Type II reactions which occur when IgM or IgG antibodies bind to antigen on the cell surface and activate the complement cascade. Granulocytes are then attracted to the site of activation, and damage from the release of lytic enzymes from their granules results in the destruction of cells. Rheumatic arthritis is thought to result from a type III hypersensitivity reaction mediated by immune complexes of antigen (in this case rheumatoid factor, an IgM autoantibody) that binds to the Fc portion of normal IgG. These immune complexes participate in causing inflammation of joints and the damage characteristic of this disease. As these pathologies are mediated in part by antibodies, therapeutics which will inhibit the generation of antibody such as the LT-β-R blocking agents of this invention will be useful for treating or preventing these diseases as well.

Treatments Using LTβ-R Blocking Agents

The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment.

Doses of about 1 mg/kg of a soluble LTβ-R are expected to be suitable starting points for optimizing treatment doses.

Determination of a therapeutically effective dose can also be assessed by performing in vitro experiments that measure the concentration of the LTβ-R blocking agent required to coat target cells (LTβ-R or LT ligand-positive cells depending on the blocking agent) for 1 to 14 days. The receptor-ligand binding assays described previously in applicants copending U.S. application Ser. No. 08/505,606, filed Jul. 21, 1995, can be used to monitor the cell coating reaction. LTβ-R or LT ligand-positive cells can be separated from activated lymphocyte populations using FACS. Based on the results of such in vitro binding assays, a range of suitable LTβ-R blocking agent concentrations can be selected to test in animals.

Administration of the soluble LTβ-R molecules, anti-LT ligand and anti-LTβ-R Abs of this invention, alone or in combination, including isolated and purified forms of the antibodies or complexes, their salts or pharmaceutically acceptable derivatives thereof, may be accomplished using any of the conventionally accepted modes of administration of agents which exhibit immunosuppressive activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The soluble LTβ-R molecules, anti-LT ligand and anti-LTβ-R Abs of this invention may, for example, be placed into sterile, isotonic formulations with or without cofactors which stimulate uptake or stability. The formulation is preferably liquid, or may be lyophilized powder. For example, the soluble LTβ-R molecules, anti-LT ligand and anti-LTβ-R Abs of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and ethyl-L-glutamate (Sidman et al., *Biopolymers*, 22, pp. 547-56 (1985)); poly(2-hydroxyethyl-methacrylate) or ethylene vinyl acetate (Langer et al., *J. Biomed. Mater. Res.*, 15, pp. 167-277 (1981); Langer, *Chem. Tech.*, 12, pp. 98-105 (1982)).

Liposomes containing soluble LTβ-R molecules, anti-LT ligand and anti-LTβ-R Abs of this invention, alone or in combination, can be prepared by well-known methods (See, e.g. DE 3,218,121; Epstein et al., *Proc. Natl. Acad. Sci. U.S.A.*, 82, pp. 3688-92 (1985); Hwang et al., *Proc. Natl. Acad. Sci. U.S.A.*, 77, pp. 4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of soluble LTβ-R molecule, anti-LT ligand and anti-LTβ-R Ab release.

The soluble LTβ-R molecules, anti-LT ligand and anti-LTβ-R Abs of this invention may also be attached to liposomes containing other LTβ-R blocking agents, immunosuppressive agents or cytokines to modulate the LTβ-R blocking activity. Attachment of LTβ-R molecules, anti-LT ligand and anti-LTβ-R Abs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem. Abst. Suppl.* 16E 77 (1992)).

Advantages of Therapeutic Compositions Comprising LTβ-R Blocking Agents

The LTβ-R blocking agents of this invention are capable of selectively inhibiting immune effector mechanisms. The inhibition of antibody mediated immunity is inhibited by multiple mechanisms including the regulation of GC formation by influencing FDC function. Both antibody and cell mediated immunity are inhibited in part by regulating the expression of addressins and thus influencing lymphocyte trafficking. Thus LTβ-R blocking agents will be useful in treating conditions that are exacerbated by the activities of antibodies, or aberrant expression of addressins. The ability to selectively inhibit such immune mediated responses will be useful for treating abnormalities including various autoimmune and chronic inflammatory conditions. As discussed above, treatment of such pathologic immune mediated conditions generally employs immunomodulatory and immunosuppressive agents which have pleiotropic effects on a wide variety of cell types and immunological responses. These non-specific immunosuppressive agents are generally required in high and often cytotoxic doses that cause adverse side effects.

The ability of a reagent which inhibits antibody responses to ameliorate a pathologic immunological response is supported in the recent study of mouse lupus nephritis. In the latter study, administration of an antibody that blocks the CD40/CD40L pathway was shown inhibit the acceleration of lupus nephritis produced upon transfer of cells which induce the production of pathogenic antibodies in vivo, and have a sustained beneficial effect on spontaneous disease long after the antibody had been cleared from the system. These data indicate that the LTβ-R blocking agents of this invention will be useful in suppressing cellular rejection of tissue grafts and organ transplants by inhibiting processes leading to the generation of antibody responses.

The LTβ-R blocking agents of the compositions and methods of this invention can be modified to obtain a desirable level of LTβ-R signalling depending on the condition, disorder or disease being treated. It is envisioned that the absolute level of LTβ-R signalling can be fine-tuned by manipulating the concentration and the affinities of the LTβ-R blocking agents for their respective molecular targets.

For example, in one embodiment of this invention, compositions comprising soluble LTβ-R molecules are administered to a subject. The soluble LTβ receptor can effectively compete with cell surface LTβ receptors for binding surface LT ligands. The ability to compete with surface LT ligands depends on the relative concentrations of the soluble and the cell surface LTβ-R molecules, and on their relative affinities for ligand binding.

Soluble LTβ-R molecules harboring mutations that increase or decrease the binding affinity of that mutant soluble LTβ-R with surface LT ligand can be made using standard recombinant DNA techniques well known to those of skill in the art. Large numbers of molecules with site-directed or random mutations can be tested for their ability to act as LTβ-R blocking agents using routine experimentation and the techniques described herein.

Similarly, in another embodiment of this invention, antibodies directed against either the LTβ receptor or one or more of the LT ligand subunits function as LTβ-R blocking agents. The ability for these antibodies to block LTβ receptor signalling can be modified by mutation, chemical modification or by other methods that can vary the effective concentration or activity of the antibody delivered to the subject.

The ability to diminish LTβ-R signalling without completely inhibiting it may be important for establishing or maintaining reduced levels of LTβ-R signalling that support normal immune function while inhibiting antibody or cell mediated responses which are exaggerated or abnormal.

Disruption of the LTα gene in a mouse leads to aberrant peripheral lymphoid organ development (De Togni et al., Science, 264, pp. 703-707 (1994)). Such mice lacked lymph nodes and their spleens lacked the usually clear demarcation between T and B cell-rich regions in the follicles. We believe that this phenotype is associated with loss of surface LT-induced LTβ-R signalling because similar phenotypes have not been observed by modulating TNF-R activity. The ability to selectively or to partially block the LTβ-R pathway may thus be useful in treating abnormal development of lymphoid-like structures resulting from chronic inflammation associated with mis- or over-expression of signalling by the LTβ-R pathway.

Antibodies are critical mediators of immune responses to pathologic agents. Thus the absolute inhibition of antibody responses may not be desirable in certain circumstances. For example, antibodies are required to mediate resistance to infections by extracellular bacteria such as pneumococci and hemophilus.

The ability to influence the level of antibody generated by blocking LTβ-R signalling may be important in maximizing the beneficial results which can be achieved by treatments with the LTβ-R blocking agents of this invention.

The therapeutic methods of the invention involve selectively inhibiting responses that are dependent in whole or in part on the LT-β pathway. The particular therapeutic uses of the claimed invention depend upon the relevant etiological mechanism of either the process to be inhibited, or the medically desirable process to be promoted, as will be apparent to those of skill in the art. Thus, the methods of the invention involve, in various embodiments, administering a therapeutically effective amount of a blocking agent of the LT-β-R, or LT-β. The protein used in these methods may be either full length proteins, fragments of the protein, or fusion fragments. In other embodiments, the methods involve the administration of a soluble fragment, such as a soluble lymphotoxin-β receptor. In other preferred embodiments, the claimed invention relates to the administration of antibodies against the LT-β-R or LT-β. The blocking agents of the invention may be administered concurrently with a therapeutically effective amount of a second compound which exerts a medically desirable effect.

For example, in certain methods for the treatment of AIDS and/or HIV, one may desire to co-administer additional antiviral agents known in the art. For example, AZT, or protease inhibitors. Particularly preferred may be the administration of blocking agents of the invention, more preferably, LT-β-R/IgG fusion protein, in combination with AIDS "cocktail" therapy. These drug "cocktails" involve the administration to a patient of multiple drugs to reduce the amount of virus in the patient's systems.

Compositions of the invention may be formulated according to standard practice, such as prepared in a carrier vehicle. The term pharmaceutically acceptable carrier refers to one or more organic or inorganic ingredients, natural or synthetic, which may facilitate the administration of the blocking agents of the invention to a patient. Suitable carriers are known to those of ordinary skill in the art.

Any of the compositions of the invention may be administered in any manner which is medically acceptable. This may include injections, by parenteral routes, such as intravenous, intravascular, intraarterial, subcutaneious, intramuscular, intratumor, intraperitoneal, intraentriculare, intraepidural, or others, as well as oral, nasal, opthalmic, rectal or topical.

sustained release administrateion is also specifically included in the invention, b means such as depot injections or implants. Localized delivery may also be diesirable. Modes of administration are easily defined by those skilled in the art.

The blocking agents of the LT pathway which are useful in the claimed invention are intended to include functional derivatives of the soluble LT-β-R, antibodies claimed herein. Functional derivatives include fragments, variants, analogs or chemical derivatives of a molecule. A fragment of a molecule, such as any of the antigens of the present invention is meant to refer to any polypeptide subset of the molecule. A variant of such molecule is meant to refer to a naturally occurring molecule substantially similar to either the entire molecule, or a fragment thereof. An analog of the molecule refers to a non-natural molecule substantially similar to either the entire molecule or a fragment thereof.

Variants of the blocking agents of the invention differ from naturally occurring agents in amino acid sequence, or in ways that do not involve sequence, or both. Variants in amino acid sequence are produced when one or more amino acids in the naturally occurring molecules is substituted with a different natural amino acid, an amino acid derivative, or a non-native amino acid. Particularly preferred variants include the naturally occurring proteins, or biologically active fragments of the naturally occurring proteins, whose sequences differ from the wild type sequence by one or more conservative amino acid substitutions. Such substitutions are well known by those skilled in the art, and typically have a minimal influence on the secondary structure and hydrophobic nature of the blocking agent.

In other embodiments, variants with amino acid substitutions which are less conservative may also result in desired derivatives, e.g., by causing changes in charge, conformation and other biological properties. Such substitutions would include for example, substitution of hydrophilic residues for a hydrophobic residues, substitution of a cysteine or a proline for another residue, substitution of a residue having a small side chain for a residue having a bulky side chain, or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Variants within the scope of the invention include proteins and peptides with amino acid sequences having at least eighty percent homology with the blocking agents of the invention. More preferably the sequence homology is at least ninety percent, or at least ninety-five percent. For the purposes of determining homology the length of comparison sequences will generally be at least 8 amino acid residues, usually at least 20 amino acid residues. Variants within the scope of the invention also include any blocking agent which 1) has an amino acid sequence which is at least forty percent homologous to the sequence of the blocking agent, and also which, 2) after being placed in an optimal alignment with the sequence of the blocking agent of the invention, has at least 80% of its cysteine residues aligned with the cysteines of the blocking agent of the invention.

Also within the invention are agents which specifically bind to the blocking agents of the invention, including ligands and antibodies.

The following are examples which illustrate the soluble LTβ receptors, anti-LT ligand and anti-LTβ-R antibodies of this invention and the methods used to characterize them. These examples should not be construed as limiting: the examples are included for purposes of illustration and the present invention is limited only by the claims.

Example 1

Preparation of Soluble Human LTβ Receptors as Immunoglobulin Fc Fusion Proteins

The sequence of a human cDNA clone isolated from a library of human 12p transcribed sequences derived from a somatic cell hybrid (Baens et al., *Genomics*, 16, pp. 214-18 (1993)), was entered into GenBank and was later identified as the sequence which encodes human LTβ-R. The sequence of this full-length human LTβ-R cDNA clone has been available since 1992 as GenBank entry L04270.

The extracellular domain of LTβ-R up to the transmembrane region (FIG. 1) was amplified by PCR from a cDNA clone using primers that incorporated Not1 and SaLI restriction enzyme sites on the 5' and 3' ends, respectively (Browning et al., *J. Immunol.*, 154, pp. 33-46 (1995)). The amplified product was cut with NotI and SaLI, purified and ligated into a NotI-linearized vector pMDR901 along with a SalI-NotI fragment encoding the Fc region of human IgG1. The resultant vector contained the dihydrofolate reductase gene and the LTβR-Ig fusion protein driven by separate promoters.

The vector was electroporated into CHO dhfr cells and methotrexate-resistant clones were isolated as per standard procedures. The LTβ-R-Ig was secreted into the medium and an ELISA assay was used to select for cell lines producing the highest level of the receptor fusion protein. A high-producing cell line was grown to large numbers and the conditioned medium collected. The pure LTβ receptor fusion protein was isolated by Protein A Sepharose Fast Flow affinity chromatography (Pharmacia).

Example 2

Preparation of Soluble Murine LTβ Receptors as Immunoglobulin Fusion Proteins

A complete cDNA clone of the murine LTβ-R was prepared by ligating a 5' NotI/ApaLI and 3' ApaLI/NotI fragments from two partial cDNA isolates into the NotI site of pcDNA3 (InVitrogen, San Diego, Calif.). The sequence of this cDNA clone is accessible as GenBank entry U29173. No coding sequence differences were noted when compared with another sequence entry for murine LTβ-R found in GenBank entry L38423.

A soluble murine LTβ-R/human IgG1 fusion protein was prepared by PCR amplification of the full length mLTβ-R cDNA clone as a template and the primers 5' AACTG-CAGCGGCCGCCATGCGCCTGCCC 3' and 5'GACTTTGTCGACCATTGCTCCTGGCTCTGGGGG 3'. The amplified product was purified and cut with NotI and Sail and ligated with a SalI/NotI human IgG1 Fc fragment into NotI-linearized and phosphatase-treated SAB132 to form JLB 122. For stable expression, the NotI cassette containing the murine LTβ-R-Ig fragment was transferred into the NotI site of pMDR901 forming PSH001 and the vector was transfected into CHO cells as described (Browning et al., *J. Immunol.*, 154, pp. 33-46 (1995)). Cell clones secreting murine LTβ-R-Ig were identified by ELISA analysis. The purified receptor fusion protein was isolated from CHO cell supernatants by Protein A Sepharose Fast Flow chromatography (Pharmacia) and is utilized in the examples which follow.

Example 3

Immunohistochemical Analysis of Spleen Following Multiple Injections of Mice with LTβ-R-Ig 4-5 week old mice received six injections, one per week, of LTβ-R-Ig or LFA-3-Ig (100 μg ip), and were immunized with SRBC on the day of the sixth fusion protein injection. Mice then received an additional injection of LTβ-R-Ig or LFA-3-Ig on day 4 after challenge with SRBC. The animals were sacrificed on day 10 after challenge with SRBC and organs were harvested for analysis of structure. The left column of FIG. 2 represents spleen sections from animals treated with LFA-3-Ig (A, C, E, G, I) and the right column from animals treated with LTβ-R-Ig (B, D, F, H, J). Acetone-fixed frozen spleen sections were double stained with biotinylated anti-mouse B220 labeled and anti-mouse CD4 antibodies (A and B), followed by a corresponding second staining with alkaline phosphatase-labeled streptavidin (purple blue, dark staining) and horseradish peroxidase-labeled mouse anti-rat Ig with (light brown staining), respectively. Another set of frozen sections were stained with ER-TR-9 (to detect MZM, C and D), MOMA-1 (to detect metallophilic macrophages, E and F), MECA-367 (specific for MAdCAM-1, G and H), and ER-TR-7 (to stain reticular fibroblasts, I and J) antibodies, followed by a second staining with a horseradish peroxidase-labeled mouse anti-rat Ig (brown staining). These pictures are representative staining of sections from a minimum of six animals. Magnification 10×.

Example 4

Effect of LTβ-R-Ig and Anti-CD40 Ligand on GC Formation and FDC Staining

Animals were treated as described in example 3 with LTβ-R-Ig or LFA-3-Ig. Another group of animals was treated with MR1 (anti-mouse CD40 ligand, 250 μg/injection, intraperitoneally) on day −1, day 1 and day 3, received SRBC on day 0 and were killed on day 10. Acetone-fixed spleen sections of animals treated with LFA-3-Ig (FIG. 3 left column, A and D), or LTβ-R-Ig (middle column, B and E), or MR1 (right column, C and F) were stained with biotin-labeled peanut agglutinin (PNA, upper row, A, B and C) or with FDC-M1 (lower row, D, E and F), followed by a second staining with a horseradish peroxidase-labeled streptavidin and horseradish peroxidase-labeled mouse anti-rat Ig, respectively (brown staining). PNA staining of the marginal zone is indicated by an arrow in A and C. GC formation is indicated by a white star in A. Staining for FDC is indicated by a black arrow in D and F. These pictures are representative staining of sections from at least four animals. Magnification 10×.

Example 5

Addressin Expression in LN of Mice Treated in Utero and Continuously Post-Birth with LTβ-R-Ig These experiments used the progeny of timed pregnant Balb/c mice which were injected iv on days 14 and 17 of gestation with 200 μg of receptor-Ig proteins. After birth the progeny were injected ip once per week with 100 ug of LTβ-R-Ig, TNF-R55—Ig, or LFA-3-Ig. Fusion protein levels remained at or above 10 μg/ml throughout life as determined by ELISA (data not shown). FIG. 4: Panels A, B, G, H staining of lymph nodes from mice treated with LTβ-R-Ig. Panels C,D staining of lymph nodes from mice treated with LFA-3-Ig, Panels E,F staining of lymph nodes from mice treated with TNF-R55—Ig. Panels A,C,E,G are mesenteric lymph nodes stained with the antibody MECA367 to detect the mucosal addressin, MAdCAM-1.

Panels B,D,F,H are peripheral (brachial) lymph nodes stained with the antibody MECA79 specific for peripheral LN addressins (PNAds). Panels G,H are lymph nodes from 6 week old mice exposed to LTβ-R-Ig in utero only. All images are 50× magnification.

Example 6

Lymphocyte Positioning and Expression of Macrophage Markers in LN of Mice Treated in Utero and Continuously Post-Birth with LTβ-R-Ig Mice were treated in utero and continuously postbirth as described for example 5 with LTβ-R-Ig, TNF-R55-Ig, or LFA-3-Ig. LN sections were then stained with antibodies specific for markers expressed by macrophages or with mAbs specific for the B cell marker B220 and the T cell marker CD4. Image analysis was used in order to identify areas of overlap of T and B cell zones. FIG. 5: Panels A,D,G are B220/CD4 staining of LN from LTβ-R-Ig, LFA-3-Ig and TNF-R55—Ig treated mice respectively. Fluorescent images were analyzed using image analysis software. Panels B,E,H are staining for sialoadhesin and panels C,F,I are staining for MOMA-1.

Example 7

Effect of LTβ-R-Ig Treatment on the Antibody Response to SRBC

Balb/c mice were injected with either LTβ-R-Ig, human Ig or PBS as follows: FIG. 6A: mice received six injections as described for FIG. 2, example 3. Animals were bled day 7 (black bars) and day 14 (striped bars) after SRBC immunization. 6B: Animals received the fusion proteins on day −7 and day 0. SRBC were given on day 0 and the animals were bled on day 7 (black bars), day 14 (striped bars) and day 30 (white bars). 6C: Animals received the fusion proteins once on day 0, at the same time as the SRBC immunization. The blood was collected on day 7 (black bars), day 14 (striped bars) and day 34 (grey bars).

The titer of SRBC-specific IgM and IgG was determined by analyzing the sera in hemagglutination assays. The titer is defined as the reciprocal of the last serum dilution for which hemagglutination is detected and is represented on a log base 2 scale (1=dilution ¹/15 of the sera). Results are represented as the mean of 4 different animals per group with standard deviation

The invention claimed is:

1. A method for inhibiting a humoral immune response in a subject comprising administering to the subject a pharmaceutical composition comprising an effective amount of an antibody directed against surface lymphotoxin (LT) ligand, and a pharmaceutically acceptable carrier, such that a humoral immune response is inhibited.

2. The method according to claim 1, wherein the antibody directed against surface LT ligand is an antibody that binds to surface LT ligand without binding to secreted LTα.

3. The method according to claim 1, wherein the antibody directed against surface LT ligand binds to LTβ.

4. The method according to claim 3, wherein LTβ is human LTβ.

5. The method according to claim 1, wherein the antibody directed against surface LT ligand functions as an LTβR blocking agent.

6. A method for inhibiting a humoral immune response by inhibiting LT-β receptor signaling without inhibiting TNF-R signaling in a subject comprising administering to a subject a pharmaceutical composition comprising an amount of an antibody directed against surface LT ligand, and a pharmaceutically acceptable carrier, such that a humoral immune response is inhibited by inhibiting LT-β receptor signaling without inhibiting TNF-R signaling.

7. The method according to claim 6, wherein the antibody directed against surface LT ligand is an antibody that binds to surface LT ligand without binding to secreted LTα.

8. The method according to claim 6, wherein the antibody directed against surface LT ligand binds to LTβ.

9. The method according to claim 8, wherein LTβ is human LTβ.

10. The method according to claim 6, wherein the antibody directed against surface LT ligand functions as an LTβR blocking agent.

11. A method for disrupting the association of immune complexes and B cell follicles in a subject comprising administering to the subject a pharmaceutical composition comprising an amount of an antibody directed against surface LT ligand, and pharmaceutically acceptable carrier, such that the association of immune complexes and B cell follicles is disrupted.

12. The method according to claim 11, wherein the antibody directed against surface LT ligand is an antibody that binds to surface LT ligand without binding to secreted LTα.

13. The method according to claim 11, wherein the antibody directed against surface LT ligand binds to LTβ.

14. The method according to claim 13, wherein LTβ is human LTβ.

15. The method according to claim 11, wherein the antibody directed against surface LT ligand functions as an LTβR blocking agent.

16. A method of inhibiting a humoral response in a subject suffering from a hypersensitivity response, comprising administering to the subject a pharmaceutical composition comprising an effective amount of an antibody directed against surface LT ligand, and a pharmaceutically acceptable carrier, such that a humoral response is inhibited.

17. The method according to claim 16, wherein the antibody directed against surface LT ligand is an antibody that binds to surface LT ligand without binding to secreted LTα.

18. The method according to claim 16, wherein the antibody directed against surface LT ligand binds to LTβ.

19. The method according to claim 18, wherein LTβ is human LTβ.

20. The method according to claim 16, wherein the antibody directed against surface LT ligand functions as an LTβR blocking agent.

21. The method of claim 16, wherein the hypersensitivity response is a type I response.

22. The method of claim 16, wherein the hypersensitivity response is a type II or type III response.

23. A method of inhibiting a humoral response associated with graft rejection in a subject comprising administering a pharmaceutical composition comprising an effective amount of an antibody directed against surface LT ligand, and a pharmaceutically acceptable carrier, such that the humoral immune response associated with graft rejection is inhibited.

24. The method according to claim 23, wherein the antibody directed against surface LT ligand is an antibody that binds to surface LT ligand without binding to secreted LTα.

25. The method according to claim 23, wherein the antibody directed against surface LT ligand binds to LTβ.

26. The method according to claim 25, wherein LTβ is human LTβ.

27. The method according to claim 23, wherein the antibody directed against surface LT ligand functions as an LTβR blocking agent.

28. A method for inhibiting a humoral immune response in a subject comprising administering a pharmaceutical composition comprising an antibody directed against surface LT ligand, and a pharmaceutically acceptable carrier, such that the humoral immune response is inhibited.

29. A method for inhibiting a humoral immune response by inhibiting LT-β receptor signaling without inhibiting TNF-R signaling in a subject comprising administering a pharmaceutical composition comprising an antibody directed against surface LT ligand, such that the humoral immune response is inhibited by inhibiting LT-β receptor signaling without inhibiting TNF-R signaling.

* * * * *